United States Patent
Renner

(10) Patent No.: US 10,994,155 B1
(45) Date of Patent: *May 4, 2021

(54) METHOD AND SYSTEM FOR OPTIMIZED RECONSTRUCTION OF TREATMENT DOSE BASED ON INTEGRATED EXIT-TRANSIT IMAGES OF RADIATION FIELDS TAKEN DURING TREATMENT

(71) Applicant: Wendel Dean Renner, Columbia, MD (US)

(72) Inventor: Wendel Dean Renner, Columbia, MD (US)

(73) Assignee: Lifeline Software, Inc., Austin, TX (US)

( * ) Notice: Subject to any disclaimer, the term of this patent is extended or adjusted under 35 U.S.C. 154(b) by 154 days.

This patent is subject to a terminal disclaimer.

(21) Appl. No.: 16/376,428

(22) Filed: Apr. 5, 2019

(51) Int. Cl.
*A61N 5/10* (2006.01)
*G16H 30/40* (2018.01)
(Continued)

(52) U.S. Cl.
CPC ............ *A61N 5/1075* (2013.01); *A61B 6/032* (2013.01); *A61B 6/4208* (2013.01); *A61B 6/583* (2013.01); *A61B 6/585* (2013.01); *A61N 5/1067* (2013.01); *G06T 7/0016* (2013.01); *G06T 11/005* (2013.01); *G16H 30/40* (2018.01);
(Continued)

(58) Field of Classification Search
CPC .............. A61N 5/1075; A61N 5/1067; A61N 2005/1076; G16H 30/40; A61B 6/032; A61B 6/4208; A61B 6/583; A61B 6/585; G06T 7/0016; G06T 11/005; G06T 2207/10081; G06T 2207/10116
See application file for complete search history.

(56) References Cited

U.S. PATENT DOCUMENTS

| 5,754,622 A | 5/1998 | Hughes |
| 6,345,114 B1 * | 2/2002 | Mackie ............... A61N 5/1048 378/65 |

(Continued)

OTHER PUBLICATIONS

Nailon, et al. "EPID-based in vivo dosimetry using Dosimetry Check: Overview and clinical experience in a 5-yr study including breast, lung, prostate, and head and neck cancer patients." J Appl. Clin. Med. Phys., vol. 20, No. 1 (Jan. 2019), pp. 6-16. doi: 10.1002/acm2.12441.

(Continued)

*Primary Examiner* — Gregory M Desire
(74) *Attorney, Agent, or Firm* — Rosenberg, Klein & Lee

(57) ABSTRACT

An optimized method and system to compute the dose to a patient (2) given a captured integrated exit-transit image (5) of the radiation rays (4) traveling from the source of x-rays (1) through the patient (2) to the imaging device (3) to product the exit-transit image (5). Each radiation field image (5) is transformed (6,8,10,12) to multiple images (7,9,11,13) for each phantom thickness (26) that was measured with the imaging device (3) for a range of field sizes (21). Given the water equivalent path (22) through the patient for a ray (4) reaching a pixel (15, 16), the final pixel value (19) is interpolated from the images (9, 11) that bracket the water equivalent path through the patient (22). Adaptive feedback calibration measures are carried out effectively ameliorate the detrimental effects of off axis attenuation of pixel values.

20 Claims, 15 Drawing Sheets

(51) Int. Cl.
*G06T 11/00* (2006.01)
*G06T 7/00* (2017.01)
*A61B 6/00* (2006.01)
*A61B 6/03* (2006.01)

(52) U.S. Cl.
CPC ............... *A61N 2005/1076* (2013.01); *G06T 2207/10081* (2013.01); *G06T 2207/10116* (2013.01)

(56) References Cited

U.S. PATENT DOCUMENTS

| | | | |
|---|---|---|---|
| 6,438,202 B1 | 8/2002 | Olivera et al. | |
| 6,636,622 B2* | 10/2003 | Mackie | A61N 5/1048 378/145 |
| 7,907,697 B2* | 3/2011 | Maltz | G06T 11/005 378/7 |
| 7,945,022 B2* | 5/2011 | Nelms | A61N 5/1071 378/65 |
| 8,351,572 B1 | 1/2013 | Renner | |
| 8,605,857 B1 | 12/2013 | Renner | |
| 9,205,280 B2* | 12/2015 | Bertram | G06T 7/0012 |
| 9,480,861 B2* | 11/2016 | Kapatoes | A61N 5/1071 |
| 2013/0272593 A1* | 10/2013 | Lee | G06T 7/0012 382/131 |
| 2017/0004267 A1* | 1/2017 | Svatos | G06N 7/005 |

OTHER PUBLICATIONS

Renner, et al. "A method for deconvolution of integrated electronic portal images to obtain incident fluence for dose reconstruction." J Appl. Clin. Med. Phys., vol. 6, No. 4 (Nov. 2005), pp. 22-39. doi: 10.1120/jacmp.v6i4.2104.

Wendling, et al. "Accurate two-dimensional IMRT verification using a back-projection EPID dosimetry method." Med. Phys., vol. 33, No. 2 (Feb. 2006), pp. 259-273. doi: 10.1118/1.2147744.

Wendling, et al. "A simple backprojection algorithm for 3D in vivo EPID dosimetry of IMRT treatments." Med. Phys. vol. 36, No. 7 (Jul. 2009), pp. 3310-3321. doi: 10.1118/1.3148482.

* cited by examiner

METHOD AND SYSTEM FOR OPTIMIZED RECONSTRUCTION OF TREATMENT DOSE BASED ON INTEGRATED EXIT-TRANSIT IMAGES OF RADIATION FIELDS TAKEN DURING TREATMENT

BACKGROUND OF THE INVENTION

This invention relates to the radiation therapy applied to patients who are typically treated for cancer or other ailments with high energy x-rays from medical linear accelerators. The invention is directed to a method and system for optimized reconstruction of the dose the patient has received, using as input the radiation fields measured during treatment on the exit side of the patient with an imaging system capable of integration or a radiation detector array. This information may be used as a quality control measure of the treatment to avoid errors, by comparing the reconstructed dose to the intended planned dose.

Systems for methods treatment dose reconstruction are known. They include those disclosed in Applicant's prior U.S. Pat. Nos. 8,351,572 and 8,605,857. The efficacy and reliability of such known systems and methods, however, are diminished in varying degrees due largely to the scattering effects of radiation at points of radiation detection off the given radiation beam's central axis. For example, the resulting attenuation at such off-axis points are not adequately accounted for in the treatment dose reconstruction systems and methods heretofore known. As the radiation beam field width on the detection plane is increased, and as the patient's anatomy being radiated increases in thickness, the treatment dose reconstruction tends to become less consistent and reliable, prohibitively so beyond certain tolerable field widths and/or thicknesses for a given set of treatment conditions.

SUMMARY OF THE INVENTION

An object of the invention is to provide for converting the exit images taken during patient treatment to an in-air x-ray (or other radiation) intensity fluence map which are of a form that can then be employed to compute the dose to the patient using a dose computation system, and to do so with a consistent degree of accuracy for off-axis points of radiation detection in the exit images.

These and other objects are attained by a method formed in accordance with an embodiment of the present invention. The method provides optimized reconstruction of a treatment dose delivered to a patient during radiation therapy based on exit images captured therefrom. The method includes establishing a plurality of reference exit images measured on a detection plane by a first radiation detector through a phantom for a range of treatment field sizes and a range of water equivalent thicknesses for the phantom to emulate one or more patients. A plurality of predetermined intensity references are established for the detection plane, for the various ranges of treatment field sizes and water equivalent thicknesses for the phantom. A deconvolution kernel is determined for each of the water equivalent thicknesses of the phantom. A first radiation detector is used to capture a plurality of exit images for a plurality of the treatment fields upon a patient during radiation therapy thereof, with each exit image defined by a plurality of detection points offset from a central axis of the detection plane by a corresponding radius, the detection points each having an exit image value associated therewith. For each detection point of each exit image, there is defined at least one water equivalent path of radiation from a source to the detection point through the patient, where the water equivalent path is defined based upon predetermined image data established for the patient. A deconvolution is executed for each exit image with at least one deconvolution kernel to generate an in air radiation intensity fluence map corresponding thereto, each in air radiation intensity fluence maps being indicative of treatment dose to the patient. An adaptive calibration is selectively executed to generate a plurality of attenuation factors for at least a portion of the detection points of each exit image based on corresponding portions of the in air radiation intensity fluence map and predetermined intensity references. Responsive to the execution of adaptive calibration, the attenuation factors are selectively fed back for application to each exit image and re-execution of the deconvolution thereon to generate final in air radiation intensity fluence map therefor. A corresponding contribution to the treatment dose delivered to the patient is determined for each final in air radiation intensity fluence map of an exit image. In accordance with certain though not necessarily all embodiments, the method also includes a base attenuation correction executed to apply a plurality of base attenuation factors to at least a portion of the detection points of each exit image, the base attenuation factors being generated based on at least one of the reference exit images for a water equivalent path corresponding to the exit image.

In accordance with certain though not necessarily all embodiments, the predetermined intensity references are computed based on measurement on the detection plane by a second radiation detector through the phantom, the second radiation detector being greater in accuracy than the first radiation detector.

In accordance with certain though not necessarily all embodiments, the adaptive calibration includes for each treatment field size and each water equivalent thickness of the phantom, dividing the exit image values of the detection points by a predictive compensation factor; and, for each water equivalent thickness of the phantom, fitting a point spread function with respect to the exit image values of the detection points at each radius equaling one of the treatment field sizes, and computing in air radiation intensity fluence maps based thereon for a largest of the treatment field sizes. The adaptive calibration further includes generating a set of attenuation curves for deriving the attenuation factors, the attenuation curves each indicating a degree of attenuation upon radiation transmission through the phantom over the range of water equivalent thicknesses thereof, the attenuation curves respectively corresponding to an incremental set of detection point radius values.

In accordance with certain though not necessarily all embodiments, the method's generation of the set of attenuation curves includes the following for each one of the detection point radius values in the incremental set:
  at each water equivalent thickness, computing a ratio of intensity between a radiation intensity measured for the detection point, with respect to the predetermined reference intensity corresponding to the water equivalent thickness and said one of the detection point radius values;
  computing an average ratio of intensity for each of four diagonal segments of detection points, each diagonal segment including detection points disposed between the central axis and a corner position offset therefrom by said one of the detection point radius values along both of two dimensional axes defining the detection plane;

generating for each water equivalent thickness at said one of the detection point radius values an attenuation data point based on the corresponding average ratio; and, fitting a sum of exponentials to a set of the attenuation data points for said one of the detection point radius values to generate the attenuation curve therefor.

In accordance with certain embodiments, a method is implemented for optimized reconstruction of a treatment dose delivered to a patient during radiation therapy based on exit images captured therefrom. The method includes establishing a plurality of reference exit images measured on a detection plane by a first radiation detector through a phantom for a range of treatment field sizes and a range of water equivalent thicknesses for the phantom to emulate one or more patients. A plurality of predetermined intensity references are established at the detection plane for the ranges of treatment field sizes and water equivalent thicknesses for the phantom, the predetermined intensity references being computed based on measurement on the detection plane by a second radiation detector through the phantom, the second radiation detector being greater in accuracy than the first radiation detector. A deconvolution kernel is determined for each of the water equivalent thicknesses of the phantom. A first radiation detector is employed to capture a plurality of exit images for a plurality of the treatment fields upon a patient during radiation therapy thereof, each exit image being defined by a plurality of pixels offset from a central axis of the detection plane by a corresponding radius, the pixels each having an exit image value associated therewith. At least one water equivalent path of radiation from a source to the pixel through the patient is defined for each pixel of each exit image, the water equivalent path being defined based upon certain predetermined image data established for the patient. Deconvolution of each exit image is executed with at least one deconvolution kernel to generate an in air radiation intensity fluence map corresponding thereto, the in air radiation intensity fluence maps being indicative of treatment dose to the patient. An adaptive calibration is selectively executed to generate a plurality of attenuation factors for at least a portion of the pixels of each exit image based on corresponding portions of the in air radiation intensity fluence map and predetermined intensity references. Responsive to this execution of adaptive calibration, the attenuation factors are selectively fed back for application to each exit image and re-execution of the deconvolution thereon to generate final in air radiation intensity fluence map therefor. A corresponding contribution to the treatment dose delivered to the patient is then determined for each final in air radiation intensity fluence map of an exit image.

The various objects of the present invention are also attained by a system formed in accordance with certain embodiments. The system provides for optimized reconstruction of a treatment dose delivered to a patient during radiation therapy based on exit images captured therefrom. The system generally includes a radiation source, a reference data acquisition portion, a radiation treatment imaging portion, and a data conversion portion. The reference data acquisition portion is operably coupled to the radiation source for establishing a plurality of reference exit images measured on a detection plane by a first radiation detector through a phantom for a range of treatment field sizes and a range of water equivalent thicknesses for the phantom to emulate one or more patients. The reference data acquisition portion determines for each of the water equivalent thicknesses of the phantom a deconvolution kernel. The radiation treatment imaging portion is operably coupled to the radiation source, and captures with the first radiation detector a plurality of exit images for a plurality of the treatment fields upon a patient during radiation therapy thereof. Each exit image is defined by a plurality of detection points offset from a central axis of the detection plane by a corresponding radius, the detection points each having an exit image value associated therewith. The data conversion portion is coupled to the reference data acquisition and radiation treatment imaging portions for converting the exit images to corresponding in air radiation intensity fluence maps, each in air radiation intensity fluence maps being indicative of treatment dose to the patient. The data conversion system is configured to define for each detection point of each exit image at least one water equivalent path of radiation from a source to the detection point through the patient. The water equivalent path is defined based upon predetermined image data established for the patient. The data conversion system is configured to also deconvolve each of the exit images with at least one deconvolution kernel to generate the in air radiation intensity fluence map corresponding thereto. The data conversion system selectively executes adaptive calibration to generate a plurality of attenuation factors for at least a portion of the detection points of each exit image based on corresponding portions of the in air radiation intensity fluence map and a plurality of predetermined intensity references defined at the detection plane for the ranges of treatment field sizes and water equivalent thicknesses for the phantom. Responsive to this execution of adaptive calibration, selectively feedback is made of the attenuation factors for application to each exit image and re-execution of the deconvolution thereon to generate final in air radiation intensity fluence map therefor. For each final in air radiation intensity fluence map of an exit image, a corresponding contribution to the treatment dose delivered to the patient is thereby determined.

In accordance with certain though not necessarily all embodiments, the data conversion portion executes a base attenuation correction to apply a plurality of base attenuation factors to at least a portion of the detection points of each exit image, the base attenuation factors being generated based on at least one of the reference exit images for a water equivalent path corresponding to the exit image.

In accordance with certain though not necessarily all embodiments, the predetermined intensity references are computed based on measurement on the detection plane by a second radiation detector through the phantom, the second radiation detector being greater in accuracy than the first radiation detector.

In accordance with certain though not necessarily all embodiments, the adaptive calibration executed by the data conversion portion includes:

for each treatment field size and each water equivalent thickness of the phantom, dividing the exit image values of the detection points by a predictive compensation factor;

for each water equivalent thickness of the phantom, fitting a point spread function with respect to the exit image values of the detection points at each radius equaling one of the treatment field sizes, and computing in air radiation intensity fluence maps based thereon for a largest of the treatment field sizes; and, generating a set of attenuation curves for deriving the attenuation factors, the attenuation curves each indicating a degree of attenuation upon radiation transmission through the phantom over the range of water equivalent thicknesses thereof, the attenuation curves respectively corresponding to an incremental set of detection point radius values.

In accordance with certain though not necessarily all embodiments, execution of the data conversion portion in generating the set of attenuation curves includes for each one of the detection point radius values in the incremental set execution:

at each water equivalent thickness, computing a ratio of intensity between a radiation intensity for the detection point from the in air radiation intensity fluence map of the largest treatment field size, with respect to the predetermined reference intensity corresponding to the water equivalent thickness and said one of the detection point radius values;

computing an average ratio of intensity for each of four diagonal segments of detection points, each diagonal segment including detection points disposed between the central axis and a corner position offset therefrom by said one of the detection point radius values along both of two dimensional axes defining the detection plane;

generating for each water equivalent thickness at said one of the detection point radius values an attenuation data point based on the corresponding average ratio; and, fitting a sum of exponentials to a set of the attenuation data points for said one of the detection point radius values to generate the attenuation curve therefor.

DETAILED DESCRIPTION OF THE PREFERRED EMBODIMENTS

Drawing Reference Numerals

Figure 1:
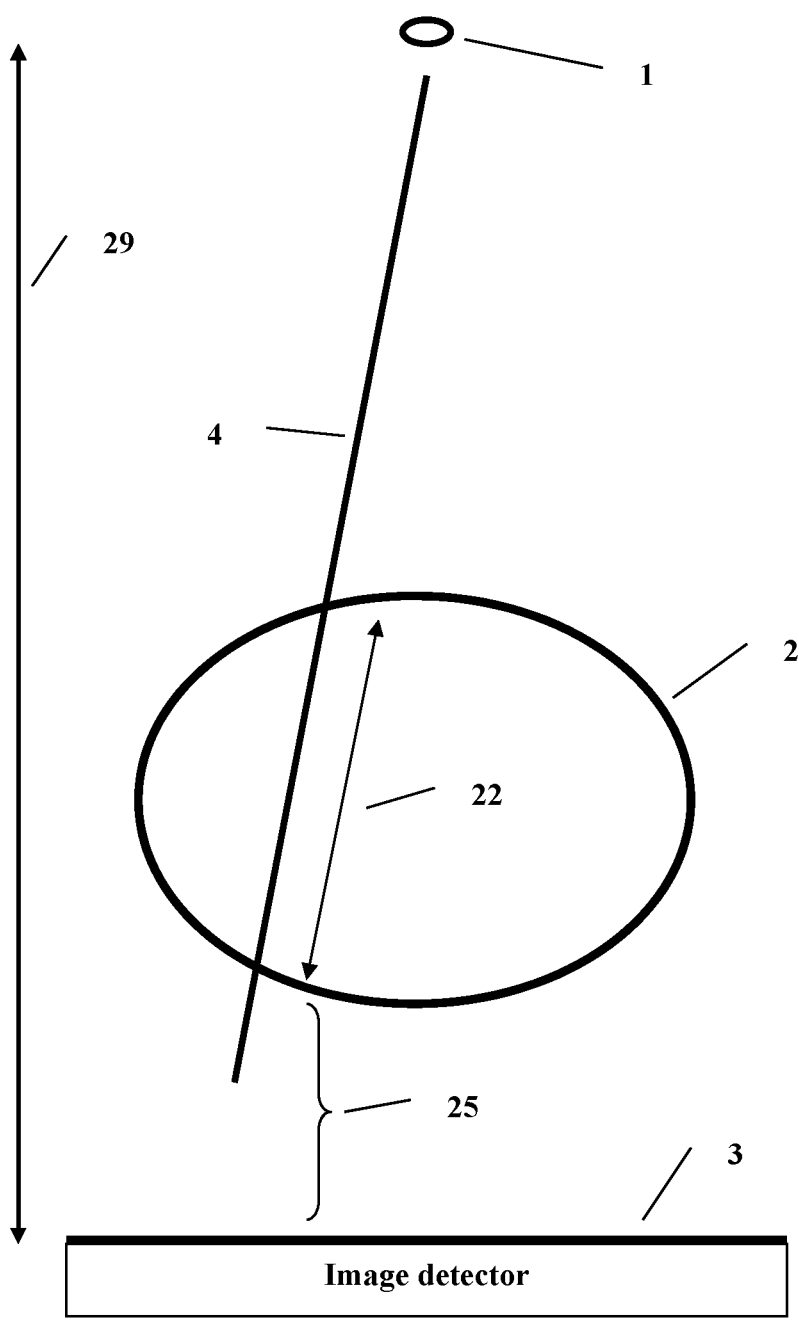
FIG. 1 is a schematic diagram illustrating an exemplary setup for measuring an exit image during patient treatment in connection with an embodiment of the present invention.

1: a source of x-rays.
2: a patient.
3: an image detector.
4: a ray from the source of x-rays to the image detector.
5: an exit image captured by the image detector.
6: a deconvolution of the image (5) to an intermediate image (7) using a kernel derived for a fixed phantom thickness (26), and in a further application for a fixed source to image detector distance (24) or phantom to image detector distance (23).
7: an intermediate image produced from the exit image (5) by deconvolution with a kernel (6).
8, 10, 12: a convolution of the image (5) to intermediate images (9, 11, 13) using the succeeding steps in thickness from the available kernels.
9, 11, 13: intermediate images produced from the deconvolution of the input exit image (5) as described above.
14: a final output image which is the in-air x-ray intensity fluence map to be used to compute the dose to the patient using a dose algorithm.
15, 16: two corresponding pixels from two intermediate images that bracket the water equivalent thickness traversed through the patient (22) to reach the corresponding pixel (19) in the exit image (5). In a further application, the interpolation would include another dimension for intermediate images with source to image distance (24) that bracket the source to image distance (29), or the air gap distance (23) that brackets the air gap (25).
17: interpolation of the input pixel values (15) and (16) to produce a final pixel value (19) in the final image (14).
19: a final pixel value interpolated between the corresponding pixel values (15) and (16).
20: a water equivalent phantom used to generate the data to fit point spread kernels for a range of phantom thicknesses (26). In certain applications, this defines different source-to-image distances (24) or air gap distances (23).
21: a collimated field size.
22: a water equivalent path through the patient (2) along a ray from the x-ray source (1) that intersects the imaging device (3).
23: an air gap distance from the phantom (20) to the image detector (3).
24: a distance from the x-ray source (1) to the image detector (3) for the reference image.
25: a distance from the exit surface of the patient (2) to the image detector (3).
26: a water equivalent thickness of the phantom (20).
27: a narrow collimated field size.
28: an ion chamber with build-up cap.
29: a distance from the x-ray source (1) to the image detector (3) for the patient exit image.
40: a medical accelerator.
41: a patient support system on which the patient lies.
42: data measured to characterize the image detector response to different thickness of water equivalent material and for different source to image distances (24) and different air gap distances (23).

43: a process of generating point response kernels for each thickness (26), source to image distance (24) and air gap distance (23).

Figure 3:
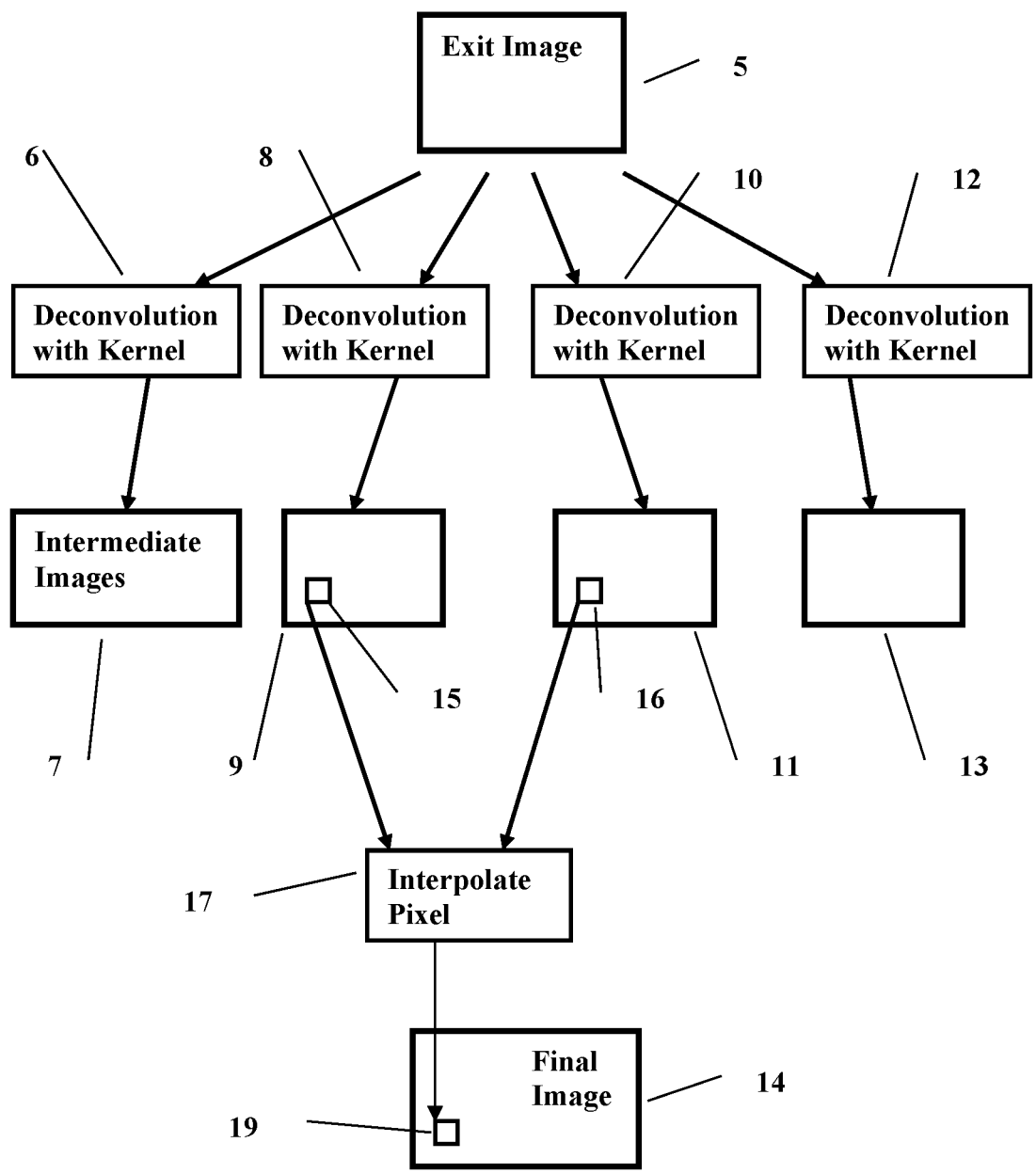
FIG. 3 is a schematic diagram illustrating a flow of processes employed in connection with an embodiment of the present invention.
Figure 6:
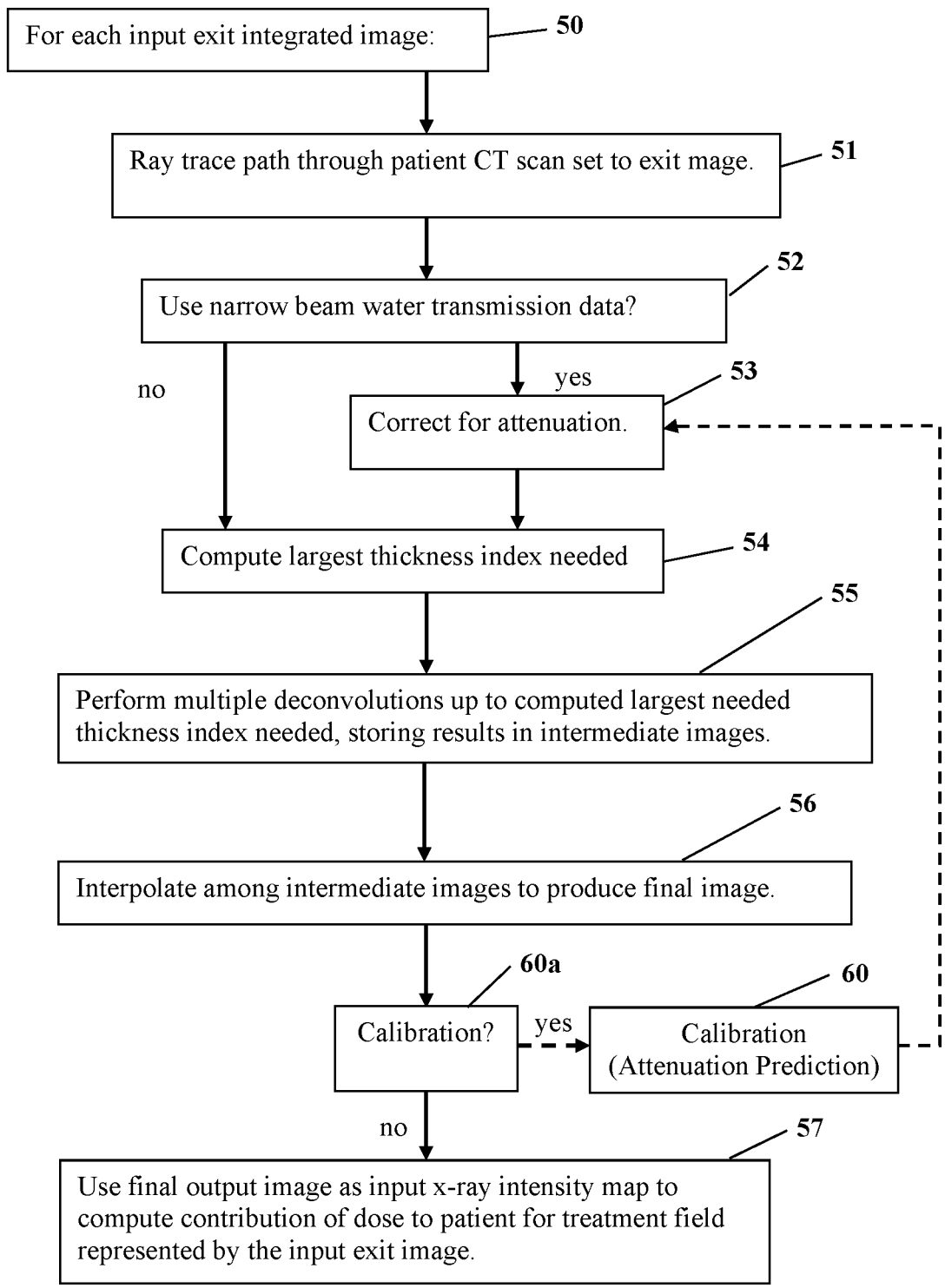
FIG. 6 is a flow diagram illustrating a flow of steps executed by a portion of the system embodiment shown in FIG. 5, as optimized in accordance with an exemplary embodiment of the present invention.

44: a process detailed in FIGS. 3 and 6 to convert patient exit images to in-air x-ray intensity fluence maps.

45: computerized tomography images that are used to model the patient's body.

46: a computation system that will compute the dose to the patient given an in-air x-ray intensity fluence map for each treatment beam.

47: a system that displays the dose computed to the patient to the practitioner.

50: part of a method flow chart, beginning of loop to process each exit image from the patient treatment.

51: part of a method flow chart, process of ray tracing the path through the patient model for each pixel on the exit image.

52: part of a method flow chart, decision on whether to correct pixel data for attenuation by the patient, based on whether the reference kernels were fitted with the data.

53: part of a method flow chart, correct pixel values by division by the attenuation of the ray reaching that pixel.

54: part of a method flow chart, process of searching the exit image to determine the maximum thickness that needs to be accounted for, to save computer time in the next operation of (55).

55: part of a method flow chart, for each point spread kernel developed from the reference images, a deconvolution process is carried out to produce an intermediate image.

56: part of a method flow chart, the process of interpolation among the intermediate images to produce a final image that represents an in-air x-ray intensity fluence map.

57: part of a method flow chart, the process of computing the dose to the patient using the final images.

The subject method and system improve upon such known methods and systems as those disclosed in Applicant's prior U.S. Pat. No. 8,351,572 and #8,605,857. By way of example, and in the interests of brevity and clarity, the preferred embodiments of the present invention herein is illustratively described with reference to various features and provisions found in these known methods and systems. As described herein with particular reference to FIGS. 6, 6A-6B, 8A-8C, and 9A-9C, the subject method and system generally optimize the accuracy of radiation treatment dose reconstruction by ameliorating the detrimental effects of off-axis radiation scattering on exit images detected through a patient's anatomy during treatment.

FIG. 1 illustrates a geometry for which an exit image is obtained during patient treatment. For brevity, exit-transit images, integrated exit-transit images, and exit-transit images are interchangeably referred to as exit images. Rays (4) from the source of x-rays (1) travel through the patient (2) along a path (22) to arrive at the image detector (3) where the intensity of the radiation is recorded along with any radiation scattered in the patient (2) that might also reach the image detector (3).

Figure 2:
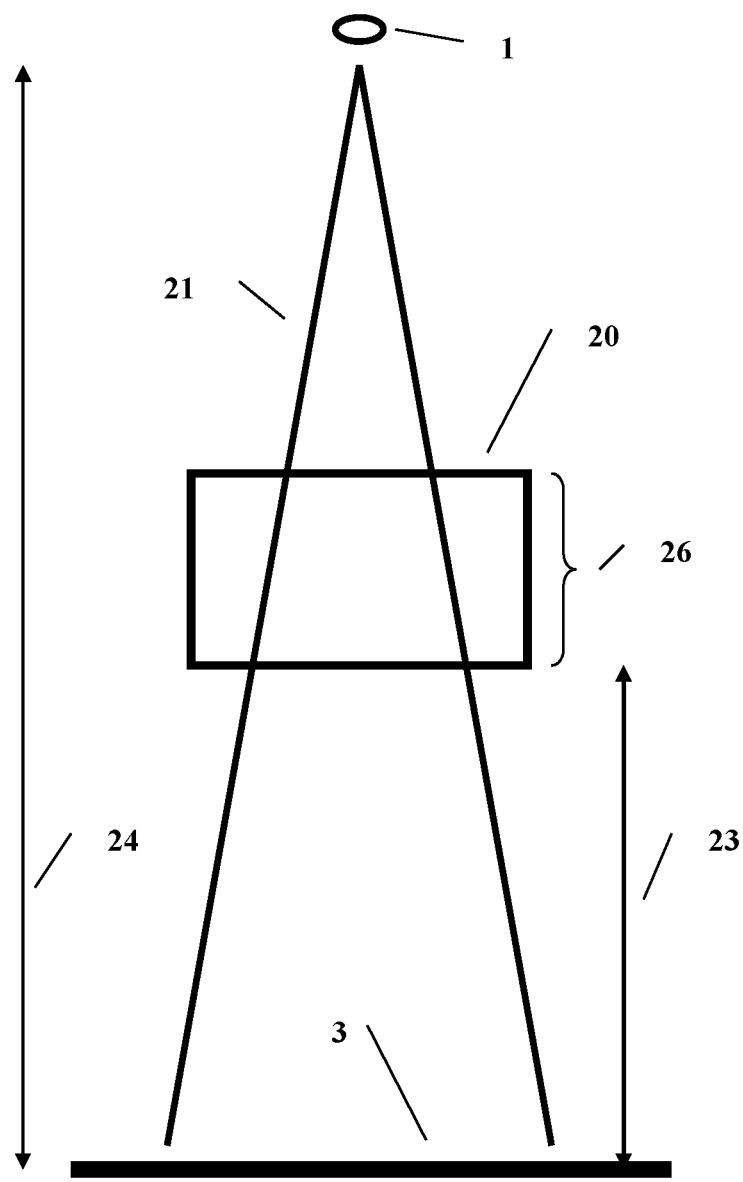
FIG. 2 is schematic diagram illustrating an exemplary setup for acquiring reference image data in connection with an embodiment of the present invention.

FIG. 2 illustrates a geometry employed to measure the data needed to implement the method. A uniformly thick water equivalent phantom (20) is placed in the beam of a radiation field collimated to a known field size (21) between the source of x-rays (1) and the image detector (3). Images are captured for a range of field sizes (21), phantom thicknesses (26), source-to-image-detector distance (24), and air gap distance (23).

FIG. 3 illustrates one example of a method for processing an input exit image. The input exit image (5) measured with the radiation detector (3) is converted by a process of deconvolution (6, 8, 10, 12) to intermediate images (7, 9, 11, 13), showing in the drawing four of a multiplicity of such images and conversions, using a look up table of point spread kernels generated from a measurement of phantom thicknesses (26) for a range of field sizes (21). In a further application of the method, the point spread kernels may be also be indexed by source to detector distance (24), or alternately the air gap distance (23). The final image (14) is produced by interpolation for the same corresponding pixels (15, 16) in the corresponding images (9, 11) that bracket the water equivalent path through the patient (22), and in a further variation would also carry out an interpolation (17) between such intermediary images that bracket the source to image detector distance (29) or air gap distance (23) of the exit image pixel.

Figure 4:
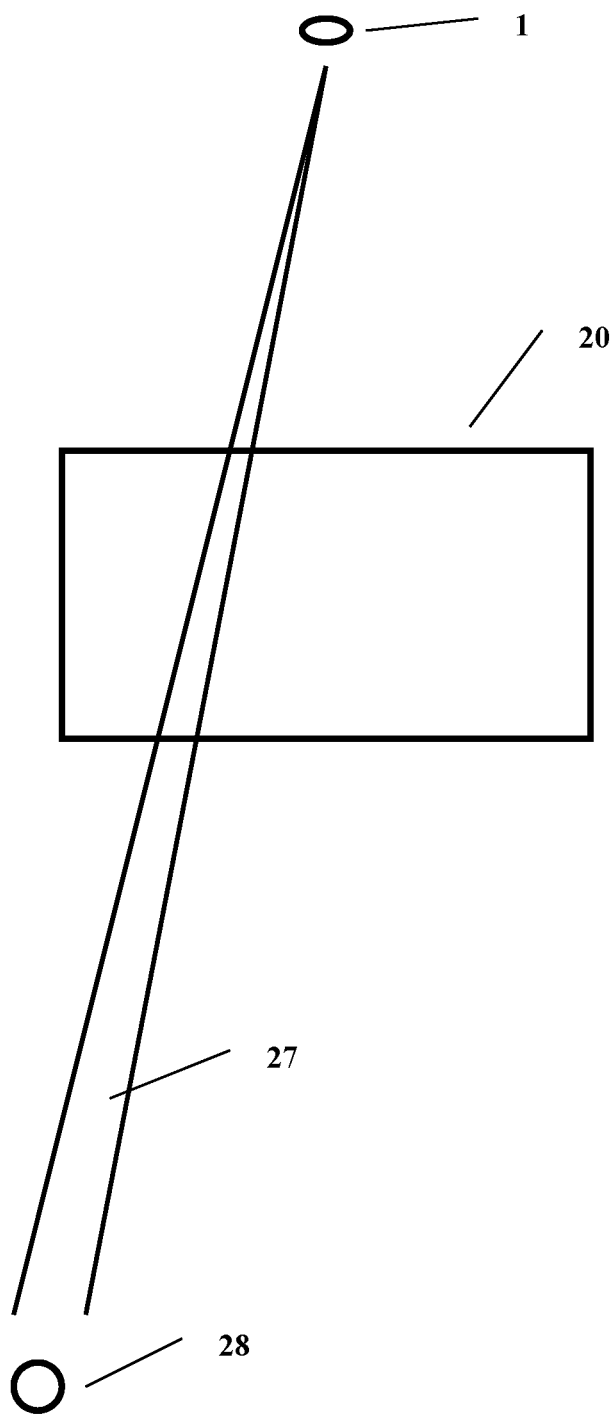
FIG. 4 is schematic diagram illustrating an exemplary setup for measuring narrow beam transmission through a water equivalent phantom in connection with an embodiment of the present invention.

FIG. 4 illustrates a geometry for measuring narrow beam transmission through a water equivalent phantom (20).

Figure 5:
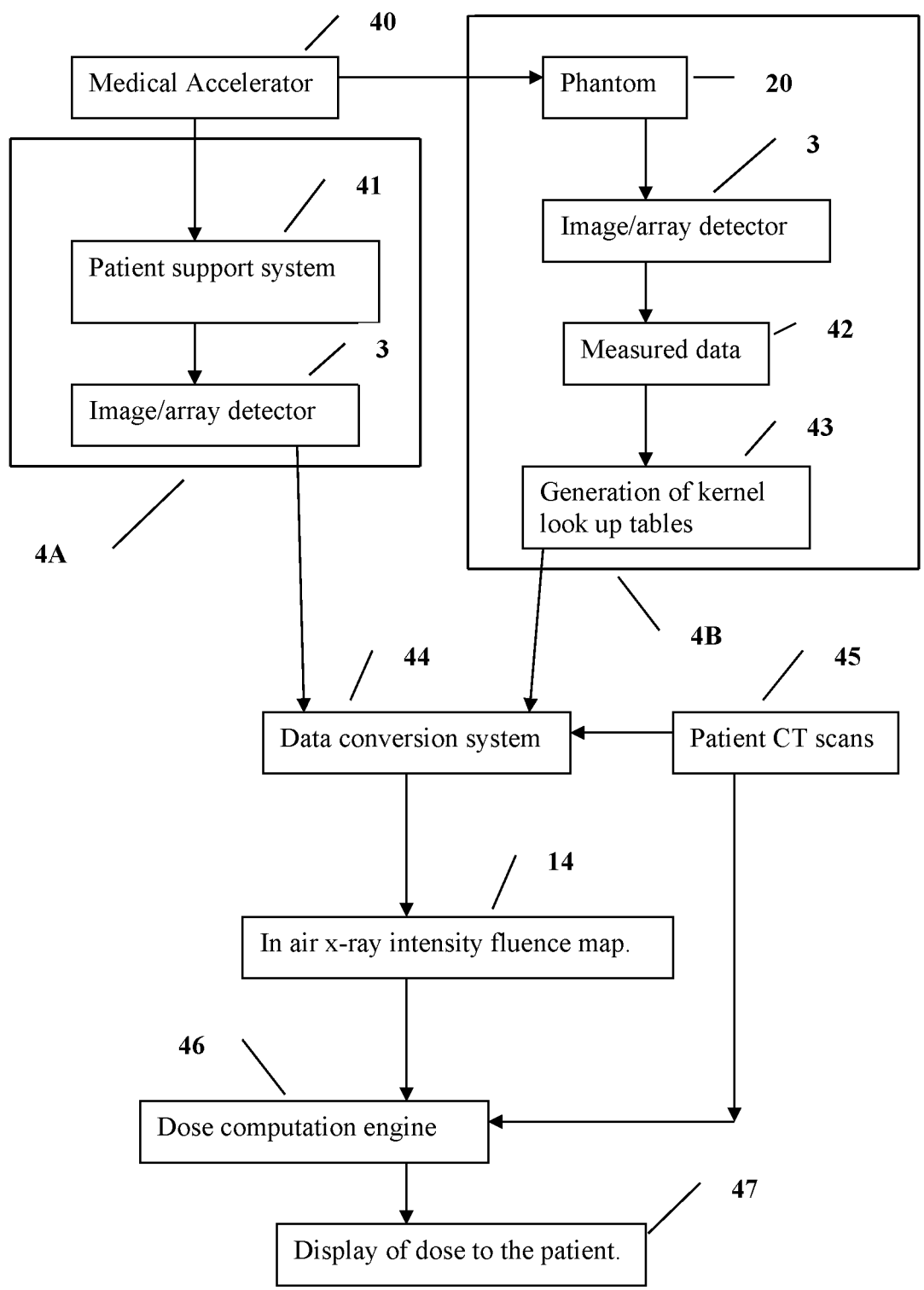
FIG. 5 is a block diagram illustrating an overall system incorporating an embodiment of the present invention.

FIG. 5 illustrates a block diagram of the operational intercoupling of functional units in an overall system in which an embodiment of the present invention is preferably incorporated. The system generally includes a radiation treatment imaging portion 4A and a reference data acquisition portion 4B. The radiation treatment portion 4A includes a suitable medical accelerator (40) which is used both to generate data described below (in portion 4B), and to generate the patient exit images (in portion 4A) in forming in-air radiation intensity fluence maps (preferably, in-air x-ray intensity fluence maps) that are used for computation. When used with the radiation treatment imaging portion 4A, the medical accelerator (40) is coupled to a patient support system (41) on which the patient lies during a treatment session. An image/array detector (3) is suitably disposed relative to the patient support system (41) to capture exit images during treatment, created by the radiation received from the medical accelerator (40) upon passage through and about the patient.

When used for the reference data acquisition portion 4B, the medical accelerator (40) is operably coupled and employed with the image/array detector (3) (preferably the same detector (3) employed in portion 4A) during a non-treatment, reference data acquisition process as described herein. A reference data measurement unit (42) is employed with the medical accelerator (4) and image/array detector (3) to characterize the image detector response to different thickness of water equivalent material (20) and for different source to image distances (24) and different air gap distances (23) (as illustrated in FIG. 2). A processing unit (43) executes a process of generating point response kernels for each thickness (26), source to image distance (24), and air gap distance (23).

Preferably, the reference data measurement unit (42) is employed in advance of patient treatment to make the measured data available for reference, so that prompt dosage information may be generated and fed back to the user/patient as necessary. Once the image/array detector (3) has acquired the radiation data from (or during) a treatment session, a data conversion system (44) applies to the acquired data the appropriate kernel information retrieved from corresponding look-up tables or the like.

The measured data obtained by the reference data measurement unit (42) is used to generate point spread kernels.

The data conversion system (44) uses the point spread kernels to convert the patient exit images to in-air x-ray intensity fluence maps (14). In doing so, the data conversion system (44) takes into account CT scans or other computerized tomography images (45) available to model the patient's body (or the water equivalent path that a ray of radiation would traverse through the patient to reach particular parts of the image/array detector (3)).

The resulting in-air x-ray intensity fluence maps (14) are inputted to a dose computation engine (46) that computes the dose to the patient given the in-air x-ray intensity fluence map corresponding to each treatment beam. A display system (47) then displays the computed dose to the patient and/or to the practitioner.

FIG. 6 illustrates a data flow in an exemplary method established in accordance with the embodiment illustrated in FIG. 5.

The different functional units may be implemented using any suitable measures known in the art. For example, the data conversion system, dose computation engine, and other such units may be programmably implemented in one or more microprocessor based platforms served by suitable memory for data access and storage.

It is known in the art that the point response of an electronic portal imaging device (EPID) can be represented by a sum of exponentials:

$$k(r) = \sum_{i}^{n} a_i e^{-b_i r}$$

where $k(r)$ is the point spread response, r is the radius in cm of a point from a ray, and $a_i$ and $b_i$ are parameters for one of n exponentials. Preferably, the value of n is five. This information was made use of to develop a method to fit the point response parameters $a_i$ and $b_i$ from a series of open field size (21) measurements with an electronic portal imaging device (EPID) or any image or radiation array detector technology (3). The parameters of the sum of exponentials are fitted as a model so that a deconvolution with the model produces the effective in-air x-ray intensity fluence map from which the correct dose is computed. If the measured image $I_{image}$ is a result of a convolution of the input x-ray intensity fluence map $I_{fluence}$ with the point response $k(r)$, then we have mathematically for $I_{image}$:

$$I_{image} = I_{fluence} \otimes k(r)$$

where the symbol $\otimes$ designates convolution. Then the fluence can be recovered by a deconvolution process. Using the convolution theorem, $I_{image}$ is the inverse Fourier transform of the Fourier transform of $I_{fluence}$ times the Fourier transform of $k(r)$. Because of circular symmetry, the two-dimensional Fourier transform of $k(r)$, namely $K(q)$, can be given by the one-dimensional Hankel transform of $k(r)$:

$$K(q) = \sum_{i}^{n} a_i \frac{2\pi b_i}{(4\pi^2 q^2 + b_i^2)^{3/2}}$$

where q is spatial frequency in cycles per cm.

Therefore we have by the convolution relationship:

$$F(I_{image}) = F(I_{fluence}) F(k(r)) = F(I_{fluence}) K(q)$$

Once we have broken $I_{image}$ out into its spatial frequency components, we can perform a deconvolution by dividing the spatial frequency components by $K(q)$ to cancel it out, where we then have the result:

$$F^{-1}\left(\frac{F(I_{fluence})K(q)}{K(q)}\right) = F^{-1}(F(I_{fluence})) = I_{fluence}$$

However, in reality $I_{fluence}$ cannot be fully recovered because $k(r)$ is a low pass operation, and spatial frequencies attenuated to noise levels and lower cannot be recovered by an inverse operation. The deconvolution process therefore provides an approximation.

The disclosed method extends the known approach for determining the dose to the patient from images taken before the patient is in place, to images taken after the patient is in place (in situ), by fitting a series of point spread response kernels for different thicknesses (26) of intervening water equivalent phantoms (20) using the images captured by the image detector (3). The image detector is preferably any array of radiation detectors capable of measuring the radiation. The structural details of such a physical device are not part of this invention, but typical available devices are electronic portal imaging devices, ion chamber arrays, and diode arrays.

A range of field sizes (21) are imaged. An example set of field sizes (21) (in cm) would be 4×4, 6×6, 10×10, 12×12, 16×16, 20×20, and 25×25. The fields need not be square but could be rectangular or any shape for which an output factor can be measured or determined. The exact number and field sizes used may vary but in general should cover the practical range of field sizes that can be used with the image detector. Each field size will correspond to a sampling from the spatial frequency space in the frequency domain necessary for the fitting of parameters using the frequency domain as illustrated above.

A purpose here is to cover as much as possible the range of spatial frequencies encountered in clinical treatment fields. For each field size used, the dose in water or equivalent material must also be measured and known for some set distance to the water surface, depth, and monitor unit setting on the treatment machine. The phantom scatter factor is computed using a dose algorithm, and divided into the measured dose to determine an effective collimator scatter factor of the field for some point in the field area. The kernel is fitted so as to produce this factor for each of the input fields using, for example, least squares. The kernel will then necessarily convert the exit image back to in-air x-ray intensity fluence as it is fitted to produce that result.

For the set of field sizes (21), images are captured for different thicknesses (26) of an intervening water equivalent phantom (20). An example of thicknesses (26) used would be 0, 5, 10, 15, 20, 25, 30, 35, 40, 45, 50, 55, and 60 cm of water or water equivalent material but the actual choice in thicknesses to use can vary. As interpolation is preferably used (as described below) between thicknesses, the increment in thickness is suitably set to minimize interpolation error.

Referring back to FIG. 2, in a certain applications, the image detector (3) is positioned at a source-to-image-detector distance (SID) (24) that will be used for imaging the patients, and for each thickness of solid water (26) the mid-thickness is placed at the isocenter of the machine. By holding the image detector to a fixed distance (24) and centering the phantom (20) about the isocenter, one data set can be used as an approximation for all expected situations without having to consider different air gap distances (25)

between the patient and the detector, as the change in the scatter contribution is known to be a slow function of the air gap. However, another approach would be to repeat the measurements at different source to detector distances (24) or air gap distances (23) to enable a further refinement in the method to be described below.

For each given thickness (26), the series of images taken for the different field sizes (21) are used to fit a point spread function (kernel), indexed by that thickness. This series of different thicknesses will include the zero thickness, such as used in conventional pre-treatment images. The images for each thickness are all normalized to a calibration image taken with zero thickness. The calibration image is for a monitor unit exposure and field size for which a definition of the monitor unit is known in terms of distance to phantom surface, depth, and dose rate and preferably expressed in cGy/mu (centiGray per monitor unit). The point spread for each thickness is fitted so that the value on the central axis of the radiation field is converted to the expected effective collimator scatter factor for the particular open field size when doing a deconvolution of the image with the fitted point spread function. The effective collimator scatter factor is computed by dividing the measured output factor in cGy/mu by the computed phantom scatter factor for the same field size and depth. For each thickness (26), there is the result of the point spread function that can be used as a deconvolution kernel to transform the image back to an in-air x-ray intensity fluence map (14). The resulting process of converting the image back to in-air x-ray intensity fluence is therefore dependent on actually measured image data, rather than a formal computational model.

The measured image for each thickness of intervening phantom will contain the effect of the scatter reaching the imager from the phantom, and any energy response of the imaging device due to both the scatter radiation and the beam hardening from traversing the phantom. This will tend to be specific to the distance (23) by which the imager is displaced from the phantom (20). However, errors in the air gap (25) from the patient to the image detector may be suitably tolerated or compensated for in certain applications. Because the scatter contribution is a slowly changing function of air gap, the errors are expected to be small.

As a further variation, the kernels may also be generated for different air gap distances (23) by generating more images with a different phantom-to-image-detector (3) distance (23) in FIG. 2, or with varying source-to-image-detector distance (24).

As yet a further variation, the transmission of the beam off axis may be considered separately from the central axis. This is performed by first measuring narrow beam transmission as a function of off-axis distance and water equivalent thickness as illustrated in FIG. 4. This data may be collected, for example, by placing an ion chamber (28) with a suitable build-up cap (material added to the ion chamber to achieve electronic equilibrium) at a suitably large air gap distance from an intervening water tank or water equivalent material (20). A multi-leaf collimator may then be used to form a small field beam having a width (27) to progress along an axis, diagonal, or any radius, out to the corner of the largest field size available. A corner would be a point on the detection plane offset from the center by the largest field size radius in each of the two dimensions along which the plane is defined.

Alternatively, the data may be measured in an equivalent manner with a narrow column of water disposed between the ion chamber and source of x-rays, with the column shifted and the gantry rotated accordingly, so that there is only a narrow scattering volume, to measure the attenuation of succeeding off-axis rays. In all cases, each measured column is preferably converted to the thickness along the slant path through the water and then fitted to a sum of exponentials. The fit is then used to compute the transmission for any given water equivalent thickness including any needed extrapolation, and linear interpolation is performed between columns of such data. In this manner the transmission of a beam at any angle with the central axis can be computed for any given equivalent water thickness.

The narrow beam transmission fit may be employed to improve the accuracy of off-axis results since the beam transmission through the patient occurring off axis tends to be less than that occurring on the central axis. Using the transmission data, each pixel of the exit images is first corrected for transmission through the phantom before deconvolution by dividing the pixel value by the attenuation value. This correction could also be moved to after the deconvolution. Without the data, the exit image values are used directly and the attenuation will be accounted for from the deconvolution kernel. It is important that kernels fitted with the in-water transmission data be used with the in-water transmission data in converting exit images to in-air x-ray intensity fluence maps. Care is taken not to use in-water transmission data kernels which were fitted without use of this data, as illustrated at operation (53) in the flow chart of FIG. 6.

The combined point spreads for each thickness will give a deconvolution kernel as a function $k(r, th)$ of radius r indexed by thickness th, where interpolation between thicknesses can give a continuous function of thickness. For each thickness, a two-dimensional Fourier transform of $k(r,th)$, or a one-dimensional Handel transform of $k(r,th)$, will be $K(q,th)$. To perform a deconvolution in the spatial domain, one would have to use the transform of $1/K(q,th)$.

By way of example, consider the processing of each input exit image in operation (50) of the flow chart FIG. 6 captured by an image detector (3) during radiation therapy of a patient (2), the exit image being formed by an array of pixels. For each pixel in the exit image, the equivalent water thickness traversed by the ray from the source of x-rays (1) to that pixel is needed. Each ray through a model of the patient, which may be formed by the patient's corresponding CT data set, is traced to compute the water equivalent thickness traversed (22) for each pixel in the exit image. In operation (51) of the flow chart of FIG. 6, rays are traced from the source of x-rays along a path through the patient CT scan set to the pixels of the input exit image. The equivalent water thickness found from the ray trace through the patient is stored for each pixel. To save computer processing time, a coarser matrix of pixels can be ray traced with interpolation between pixels.

At operation (52) a check is made as to whether the deconvolution kernel was fitted using the in-water transmission data. If so, the attenuation value of each of the above rays is computed using the equivalent water path, and the intensity value at each pixel of the exit image is divided by the attenuation value, as indicated in the correction operation (53) of FIG. 6. If the deconvolution kernel was not fitted using the in-water transmission data, the flow proceeds to operation (54) described below in later paragraphs.

A deconvolution can then be performed, where for each pixel in the exit image the thickness traversed to reach that pixel is used as an index into the kernel value to be applied at that point in the mathematical integration process of deconvolution.

Such a kernel, however, is variant as it will depend upon the position of the deconvolution kernel relative to the image, and the convolution theorem cannot be applied. Therefore, the deconvolution cannot be adequately performed by multiplication in the frequency domain. Consequently, the fast Fourier transform would be of no use to transform images to the spatial frequency domain. This can pose a serious problem in computation time for image detectors with a large number of detectors. Exit images taken with an electronic portal imaging device after normalization to the calibration image may be reduced to a larger pixel size such as approximately 1 mm, which still may leave an image size of the order of 400×300 pixels. We would not want to lose the advantage of the high resolution available in some image detectors with any lower resolution. One millimeter is still small compared to typical pencil beam sizes of 2 to 5 mm often used for dose computation. The deconvolution in the spatial domain just described above required about 9 minutes on a 1.81 GigaHertz Intel based PC computer running Windows XP. A seven-field intensity modulated radiation therapy (IMRT) case would require approximately one hour to transform the seven fields, and an intensity modulated arc therapy (IMAT) in a case with 72 images would require over ten hours.

A one-dimensional convolution is of the order $n^2$, whereas the fast Fourier transform is of order ($n \log_2 n$). For two-dimensional images a convolution is of order $n^4$ and the fast Fourier transform is of the order $(n \log_2 n)^2$. For a 512×512 array size, using the fast Fourier transform should be about 3236/2 (the division by two from transforming each way) times faster than a discrete convolution. Preferably, the large computational time required for a discrete deconvolution in the spatial domain is eliminated by use of the following approximation, also illustrated in the flow chart of FIG. 6 and in the schematic diagram of FIG. 3.

It is assumed that there are n total thicknesses measured with the image detector resulting in n deconvolution kernels, indexed by the thickness. For a single exit image, the image is deconvolved n times for each of the n kernels using a fast Fourier transform to produce n intermediate images. There in fact is only a need to convert images up to the thickness that includes all the thicknesses traversed for a particular image, for increased efficiency. Preferably, a search is made for the maximum water thickness among all the pixels of the exit image, as indicated at operation (54) in FIG. 6. From the list of deconvolution kernels for different thicknesses (preferably sorted in order of increasing thickness starting at zero), the index number for the smallest thickness greater than the maximum thickness is computed. Let M be the index number.

At operation (55), for each deconvolution kernel from zero thickness up to and including the index number M found above, a deconvolution operation is performed on the input exit image (5) (of FIG. 3). Each such output image is stored in a list of intermediate images (7, 9, 11, 13) indexed by the thickness of the deconvolution kernel used therefor.

This part of the method is schematically illustrated in FIG. 3. The exit image (5) is deconvolved with M thicknesses, only four of which are illustrated in FIG. 3 (6, 8, 10, 12) to produce M deconvolved intermediate images (7, 9, 11, 13), with four images of a multiplicity of such images shown in FIG. 3.

Referring back to FIG. 6, in operation (56), for each pixel in the input exit image, the water equivalent thickness stored for that pixel is consulted, and the two intermediate images that bracket the thickness value are determined. The pixel value between the corresponding pixel in those two images (15) (16) is interpolated using the thickness values as the index. The interpolated value for the corresponding pixel (19) is stored in a final output image (14) such as shown in FIG. 3.

As an example to illustrate the interpolation part of the method in operation (56), if the thickness traversed for a particular pixel (19) were to be 32.0 cm, then interpolate between the output images deconvolved with thicknesses that bracket 32.0 cm. Let image (9) be from a 30 cm thickness kernel and image (11) from a 35 cm thick kernel. Then the pixel value (15) in the 30.0 cm thickness kernel and the corresponding pixel value (16) in the 35.0 cm thickness kernel are interpolated (17) to produce the value to assign to the corresponding pixel (19) in a single output image (14). Using this scheme, the time required to process the exit image to produce the in-air x-ray intensity fluence image was reduced from 9 minutes to about 1.7 seconds on the same computer (including the time for the ray trace). As the image detector point spread decreases rapidly with radius, and the patient thickness will usually be slowly varying over the area of the image, this method is a reasonable approximation to an equivalent deconvolution in the spatial domain. In a variation of the method, the ray trace can be done on a coarser grid with values interpolated in between nodes to same computer time.

In another application, the above transmission data can be used to compute the attenuation from the water equivalent path computed through the patient. The pixel values are then corrected for this attenuation. This further operation will allow correction for the x-ray penetration that is less for rays disposed farther from the central axis. The spectrum off axis changes with lower energy components and as a result the x-rays have an increased attenuation rate.

In another application of the method, additional data can be taken at different image detector distances (24) or air gap distances (23) to produce further sets of kernels, indexed also either by detector distance or by air gap distance. These kernels will add another dimension to the kernels with a corresponding interpolation of intermediate images by source-to-image-detector distance (29) or air gap (25) as the case may be.

For example, let there be images of a series of uniform thickness phantoms as before with an air gap of 50 cm (23), with a point spread kernel fitted for each thickness. Let there also be a set with an air gap of 25 cm (23). By means of interpolation, there would result a kernel that is a function of thickness and air gap, namely: k(r,th,ag) where ag is the air gap. The corresponding transform would be K(q,th,ag). In the interpolation scheme of FIG. 3 and FIG. 6 for block (56), interpolation would also be performed for the air gap. In the above example, if in addition to a path of 32 cm to a pixel of an exit image, the air gap from the patient to the image detector was 42 cm for that pixel, the final pixel value would be interpolated among the four intermediate images deconvolved with the point spread kernels for thicknesses of 30 cm and 35 cm with the air gap of 50 cm, and the intermediate images deconvolved with the point spread for thicknesses 30 cm and 35 cm with the air gap of 25 cm. Similar applications would alternatively consider the source-to-image distance instead, or as well.

As indicated at operation (57), the final output image (14) (of FIG. 3) is obtained to include an in-air x-ray intensity map which is then used directly to compute the dose to the patient from the radiation field that created the exit image. Repeating this process for each treatment field, the composite dose from all treatment fields to the patient is computed. For intensity modulated arc therapy (IMAT), the rotation is simulated by fixed treatment fields at the angles at which exit-transit images are captured. By capturing such images in small increments of angle, the resultant computed dose will be a good approximation.

Often, image detectors such as electronic portal imaging device (EPID) which are employed for reconstructing radiation treatment dose delivered to a patient from images taken during actual treatment of the patient are prone to scattering and other attenuation effects. The effects become more pronounced as radiation field size and the patient's water equivalent thickness expand. This is unlike more robust and/or higher precision detection devices like ion chamber devices, for instance, which are typically employed in controlled settings to acquire reference images (with water equivalent phantoms for instance), which exhibit relatively stable scan profiles when used to detect radiation across the off-axis range covered by the given field size. In typical treatment applications, therefore, reliability of the pixel values measured by the EPID's radiation detector arrays of the treatment radiation tends to exhibit marked drop off as field size extends farther away from the beam's central axis, and as water equivalent thickness increases.

Consequently, it is often observed in practice that as treatment beam field sizes expand beyond about 15×15 cm (in orthogonal diametric dimensions), scanned profiles of the reconstructed dose based on actual image detector measurements become less reliable. Compared to ion chamber based scans under like conditions, reconstructed dose measurements are substantially equivalent at the central axis, but drop off from the ion chamber reference at detection points moving away from that central axis. This is increasingly so with greater equivalent water thicknesses.

Figure 8A:
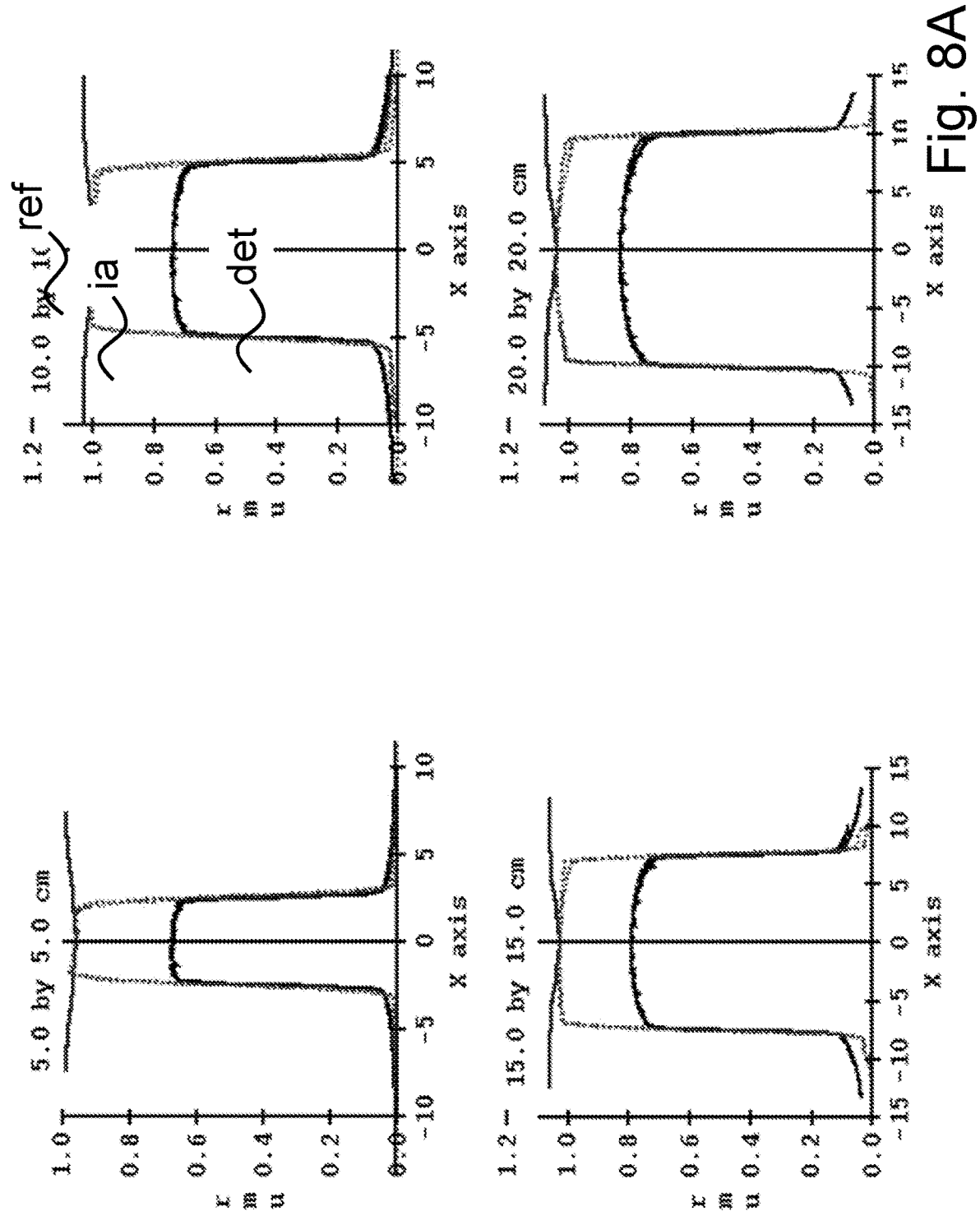
FIGS. 8A-8C are a schematic diagrams illustrating graphic plots of in air fluence profiles obtained at different radiation beam field sizes, with various water equivalent thicknesses without optimization such as provided by the calibration process of FIG. 6A; and, FIGS. 9A-9C are a schematic diagrams illustrating graphic plots of in air fluence profiles obtained at different radiation beam field sizes, with various water equivalent thicknesses with optimization such as provided by the calibration process of FIG. 6A, applied as illustrated in FIG. 6.
Figure 8B:
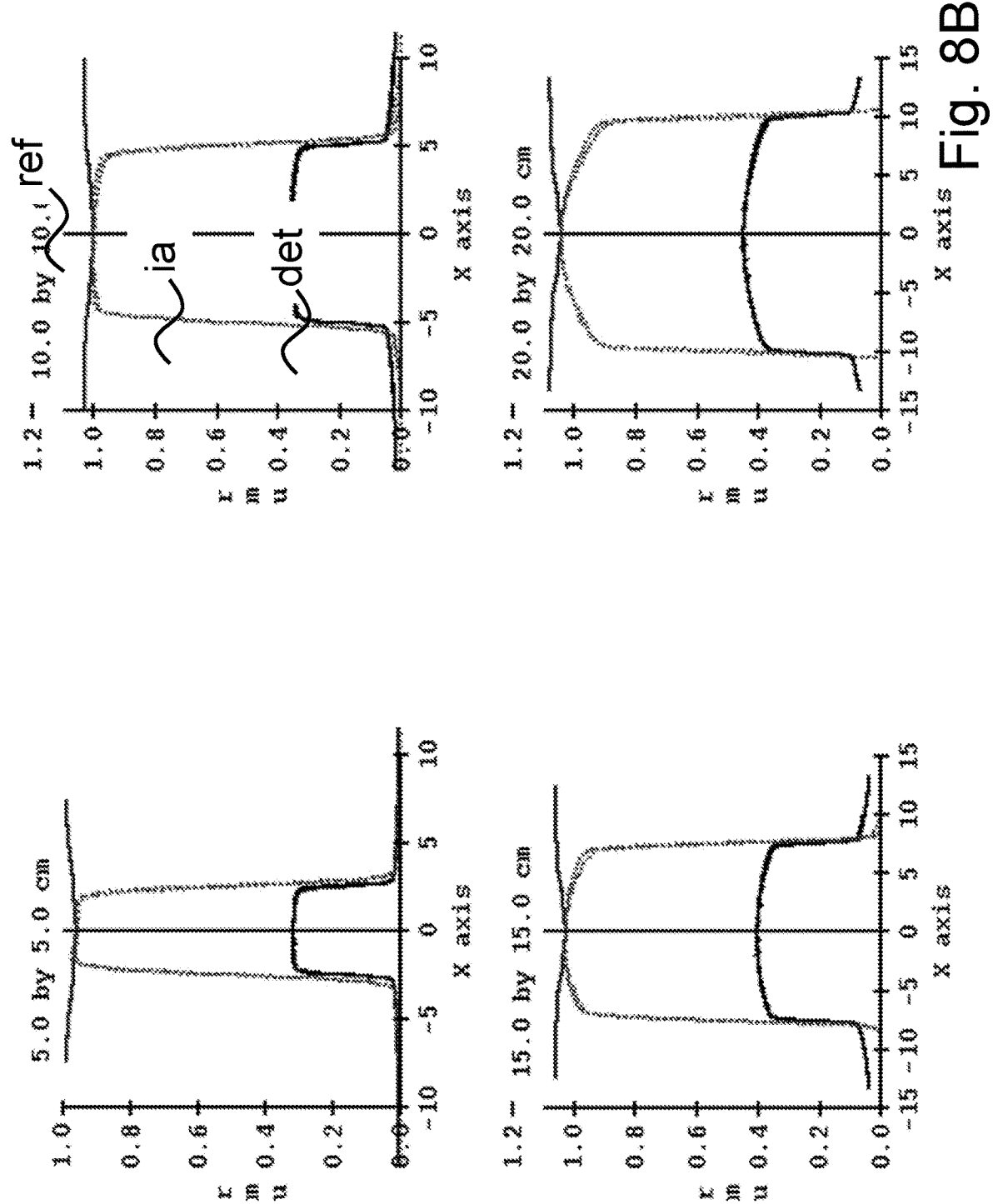
Figure 8C:
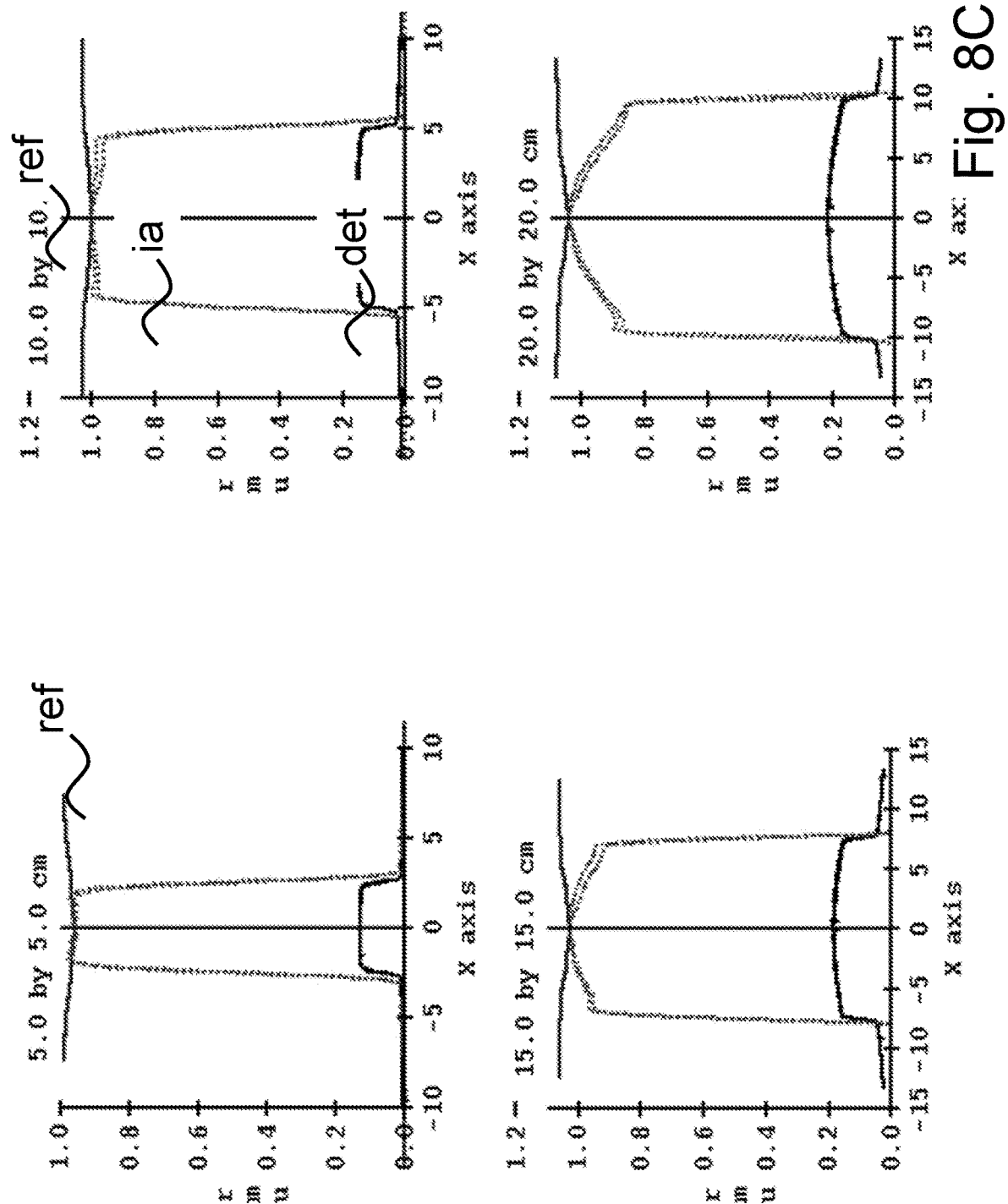

In typical applications, the observed drop off is precipitous across all water thicknesses as field size extends beyond about 15×15 cm. Examples of this are illustrated in FIGS. 1A-1C, which show in air radiation intensity fluence maps/profiles as plotted ('scanned') across one diametric dimension at the different field sizes indicated. FIGS. 8A-8C respectively illustrate the in air fluence profiles obtained for water equivalent thicknesses of 5 cm (the plots of FIG. 8A), 20 cm (the plots of FIG. 8B), and 40 cm (the plots of FIG. 8C). The various plots in each of the FIGS. 8A-8C actually show examples of profiles taken with the same water equivalent thickness, over various field sizes: for example, 5×5 cm, 10×10 cm, 15×15 cm, and 20×20 cm.

In each plot, profile ref represents the ion chamber device-measured in air profile for the given radiation machine/source, which provides a reference for the other profiles det and ia. The profile det represents the radiation measurements of the given image detector before they are converted back to in air profiles. The profile ia represents the detected radiation measurements after conversion according to a heretofore known EPID process to in air radiation intensity fluence.

As shown, with every water equivalent thickness, and with every radiation field size, the in air radiation intensity fluence profile ia correlates closely to the reference profile ref at the central axis of the radiation field. For the 5 cm water thickness case, the profiles ia remains well correlated to the reference profiles ref even at points 5 cm away from the central axis (or 10 cm diametrically). For the thicker 20 cm and 40 cm water thickness cases, however, the profiles ia begin to diverge from the reference profiles ref at points 5 cm from the central axis. At points further off-axis beyond that, the profiles ia diverge even more from the reference profile ref regardless of water thickness. The divergence is observed in these cases to be more pronounced for the greater water thicknesses. Beyond a field size of about 15×15 cm (or about 7.5 cm off-axis), for example, the profiles ia for all the water thickness cases illustrated diverge markedly from the reference profile ref.

Consequently, beyond such field sizes, the dose reconstructed from such actual image detector measurements made during patient treatment diverge sufficiently from the reference profile ref to be largely unreliable. In one exemplary embodiment, the radiation dose reconstruction is optimized for efficacy even over these larger field sizes and greater water thicknesses. The measured off axis narrow beam attenuation curves currently used for attenuation correction are replaced with those derived by the calibration process as described below.

In the processing of exit images measured during treatment, as illustrated in FIG. 6, a calibration process 60 is preferably employed once the exit image based on image detector measurements during treatment is fully generated at block at block 56 and made available. This is checked at block 60a, and if the final exit image is available, it the calibration process 60 is executed and the results fed back as illustrated to the attenuation correction process at block 53. Generally, this feedback loop provides for adaptive calibration the image pixel values obtained during treatment at block 56 to be divided, for instance, by the attenuation of the ray reaching the given pixels. The applied attenuation is adaptively derived through the calibration process 60 based in part on the measured off axis transmission data made available at block 56. The attenuation correction process 53 is then carried out again, but with the measured off axis attenuation curves directly employed otherwise replaced by substitute attenuation factors adaptively derived and fed back by the calibration process 60.

The operational flow proceeds from there again through the processes 54, 55, 56 for re-generation of a final exit image with the calibrated attenuation properly accounted for. After at least one iteration of such adaptive calibration feedback loop for attenuation correction is carried out, the flow is directed at block 60a to proceed on to block 57, where the corresponding radiation dose contribution to the patient is suitably computed based on this re-generated final exit image.

Figure 6A:
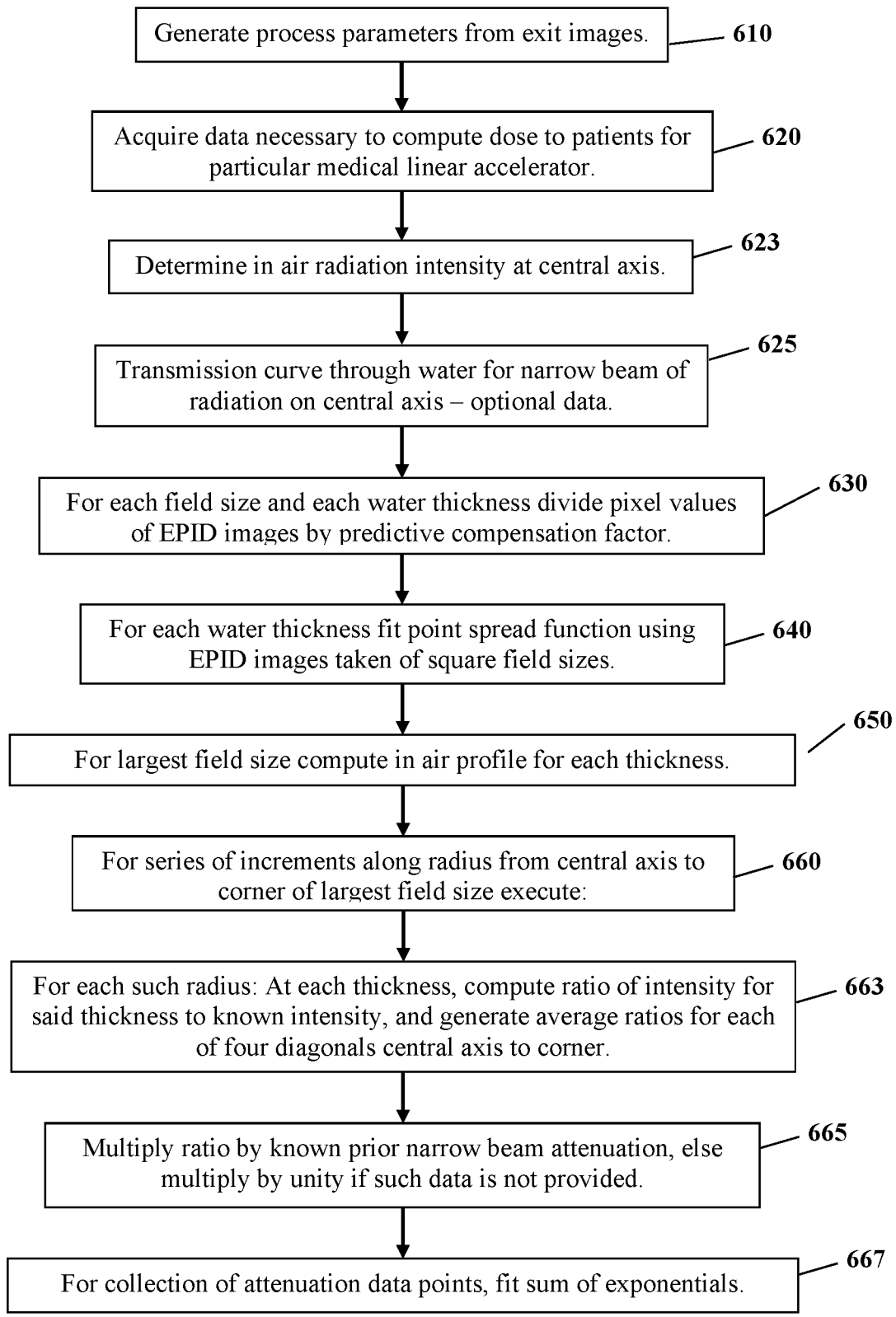
FIG. 6A is a is a flow diagram illustrating a flow of steps executed in connection with a calibration process portion of the flow shown in FIG. 6.

Referring to FIG. 6A, in accordance with certain aspects of the present invention, the calibration process 60 of FIG. 6 is preferably carried out in one exemplary embodiment as follows:

At block 610, process parameters required for attenuation correction are generated as otherwise provided according to FIG. 6 from a series of EPID reference images taken of a water phantom in the beam for a range of field sizes and a range of water thicknesses. These parameters include for example those relating to the deconvolution kernels for different equivalent water thicknesses of the phantom.

At block 620, the data needed to compute the dose to patients is initially acquired for the particular medical linear accelerator (radiation generating machine or other suitable radiation source) employed in any suitable manner known in the art. Preferably, this data includes:

an in air radiation intensity perpendicular to the central axis that is emitted from the radiation generating machine employed, as indicated at block 623;

a transmission curve through water for a narrow beam of radiation on the central axis is preferably provided as optional data, as indicated at block 625.

Depending on the particular embodiment and application, other initially acquired data used for computing dose, and which pertain to the given radiation source may include for example:

- a set of percent depth doses for a range of field sizes (such as the dose at depth on the central axis in a water phantom for a given field size at a specified distance, typically 100 cm, with a predefined range of field sizes such as 3×3 cm, 5×5 cm, 10×10 cm, 15×15 cm, 20×20 cm, 25×25 cm, 30×30 cm, 40×40 cm);
- a characteristic in air off axis ratio;
- an output factor in cGy/mu for each predetermined field size employed;
- diagonal profiles in water for the largest field size.

The Calibration Process (Blocks 630-667):

At block 630, for each field size and each water thickness, the pixel values of the EPID images are divided by a predictive compensation factor—preferably, the computed transmission through the water thickness on the central axis in the illustrated embodiment. If the narrow beam transmission is not provided, the division is by one.

At block 640, for each water thickness, a suitable point spread function is fitted using the EPID images taken of square field sizes. This is preferably carried out as described in preceding paragraphs, for instance, in connection with the point spread response k(r) which is represented as a sum of exponentials.

At block 650, for the largest field size, the in air profile for each thickness is computed for each thickness, preferably according to the processes illustrated for instance in FIG. 6.

At block 660, for a series of increments along the radius from the central axis to the corner of the largest field size (largest value in each dimension), the following is preferably executed for each such radius:

At each thickness, the ratio of the intensity is computed for that thickness to a predetermined known intensity corresponding to that thickness at the given radius. The predetermined known intensity preferably includes corresponding off axis measurements obtained using more robust and/or higher precision detection devices such as ion chamber devices or the like. An average ratio is obtained for each of the four diagonals central axis to corner, as indicated at block 663.

The ratio is multiplied by a predetermined known prior narrow beam attenuation to create a data point of attenuation versus thickness for the radius. Alternatively, the ratio is multiplied by unity (one) if such known prior narrow beam attenuation is not predetermined, as indicated at block 665.

For the collection of attenuation data points, a sum of exponentials is fitted to create an off axis attenuation curve for that radius which would best fit through the data points, the curve preferably being normalized to 1.0 for zero thickness, as indicated at block 667.

The resulting set of attenuation curves are then fed back for use in the attenuation correction process 53 of FIG. 6, for the narrow beam water transmission data when processing patient clinical images for dose reconstruction. In this manner, an adaptively calibrated attenuation correction is applied to the narrow beam water transmission data. This predictively compensates for such things as degraded reliability at off axis detection points due to the use of detection devices that are vulnerable to scattering and other attenuation effects beyond just a narrow radiation field size, especially at greater patient water equivalent thicknesses.

In accordance with certain alternate embodiments, the central axis narrow beam data may be eliminated in favor of a unity value (1) as described above. The set of attenuation curves in that case simply becomes a correction and is used for the narrow beam correction in the above and below paragraphs.

Figure 6B:
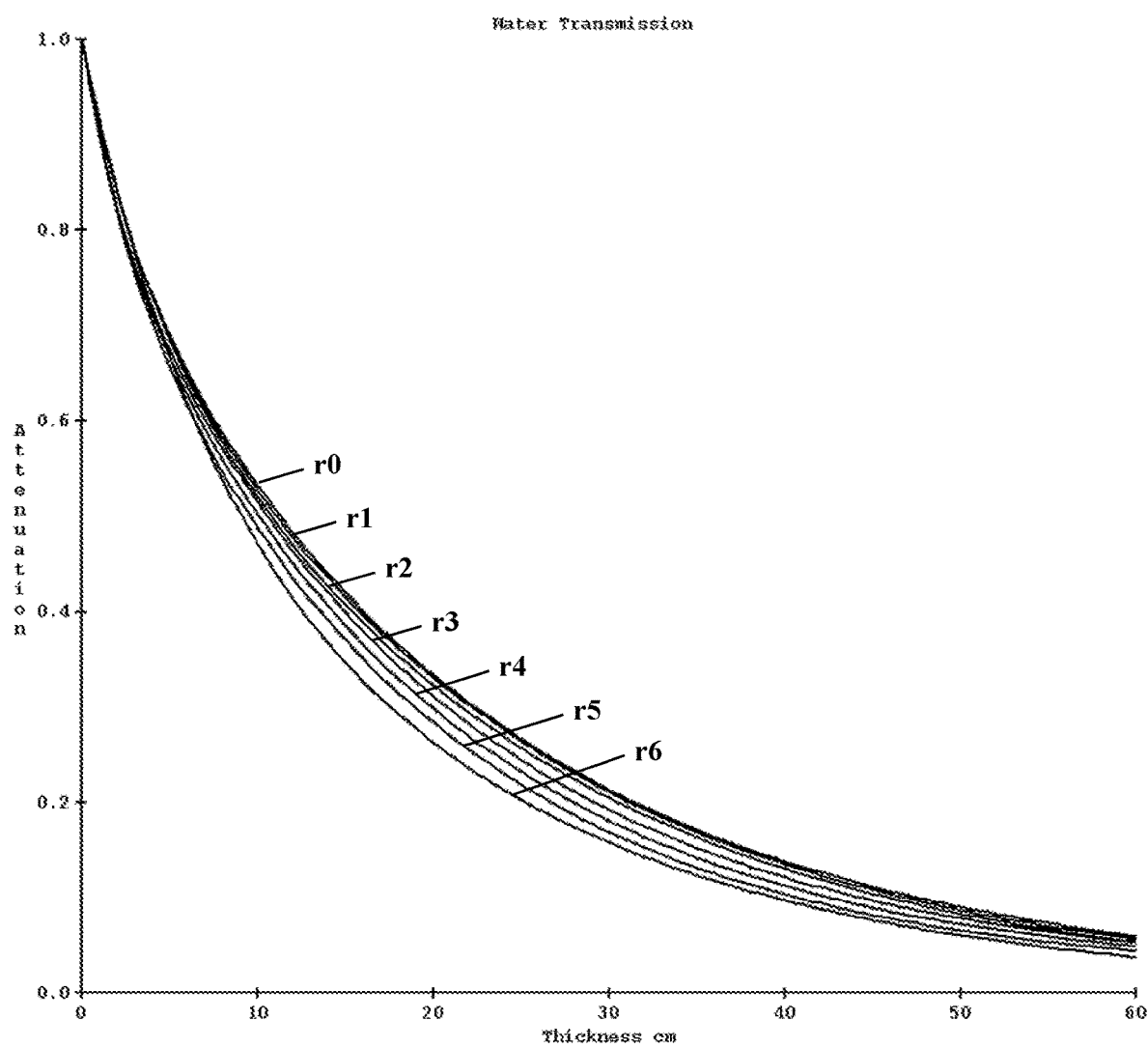
FIG. 6B is a schematic diagram illustrating a graphic plot of a set of attenuation curves generated by the calibration process of FIG. 6A.

A sample plot of attenuation versus field size for a set of radii from the central axis, as derived in the manner described by the calibration process 60, is illustratively shown in FIG. 6B. As illustrated in this sample plot, the attenuation curves—or more specifically, water transmission curves indicating the degree of transmission as attenuated over increasing water thicknesses—are illustratively generated for a graduated set of off axis radii, r1-r6. In this example, r1-r6 are set at the respective sample values: 0, 2, 5, 6, 8, 10, 12 cm from the center axis of a given radiation beam (at a distance of 100 cm from the source of radiation along the center axis).

As shown, the degree of transmission approaches unity (substantially no attenuation) at all radii as water thickness value approaches 0, and exhibits nonlinearly increasing degree of attenuation, hence nonlinearly decreasing degree of transmission, as water thickness value increases. At points on the radiation detection plane farther away radially from the central axis where the radius=0 (for example, approaching r6 and beyond), the degree of attenuation is greater (and degree of transmission lesser) for the same water thickness. Conversely, at points on the radiation detection plane closer radially to the central axis (approaching r0), the degree of attenuation is lesser (and degree of transmission greater) for the same water thickness.

In the sample plot as shown, the resolution is such that the topmost curves r0 and r1 appear darker, as the degree of attenuation for the two curves (for radius=0 cm and 2 cm off the central axis in the illustrated example) remain close and virtually coincide for the different water thicknesses. A notable separation is observed between the remaining attenuation curves down to the bottommost curve r6 (radius=12 cm off the central axis in the illustrated example).

What results is a set of fitted off axis corrections for the treatment beam as a function of thickness indexed by radius, to be then used in place of the prior measured off axis transmission in generating the in air fluence profile for use in radiation dose reconstruction for a given treatment session. In cases where no off axis measurement of the beam is available, the fitted off axis correction for the beam radius may be used in the deconvolution process where the off axis measurement would have otherwise been used. As before, the off axis corrections are interpolated between the indexed radii.

Note that in certain known dose reconstruction methods and systems, the fit of the EPID deconvolution kernels is done only for points on the central axis. That is not changed in accordance with this embodiment. In the illustrated embodiment, the off axis points after fitting the EPID deconvolution kernels are used to fit off axis attenuation curves. Those curves are then used in place of the measured attenuation curves (narrow beam transmission curves) to compute the attenuation factor using the water equivalent path length of the rays from the source of radiation to the pixels on the EPID images. Each such EPID pixel is divided by the corresponding computed attenuation factor. The water equivalent path is determined from examining the geometry of the patient model, derived from CT scans of the patient, relative to the x-ray source and EPID, as in known dose reconstruction methods and systems.

Figure 9A:
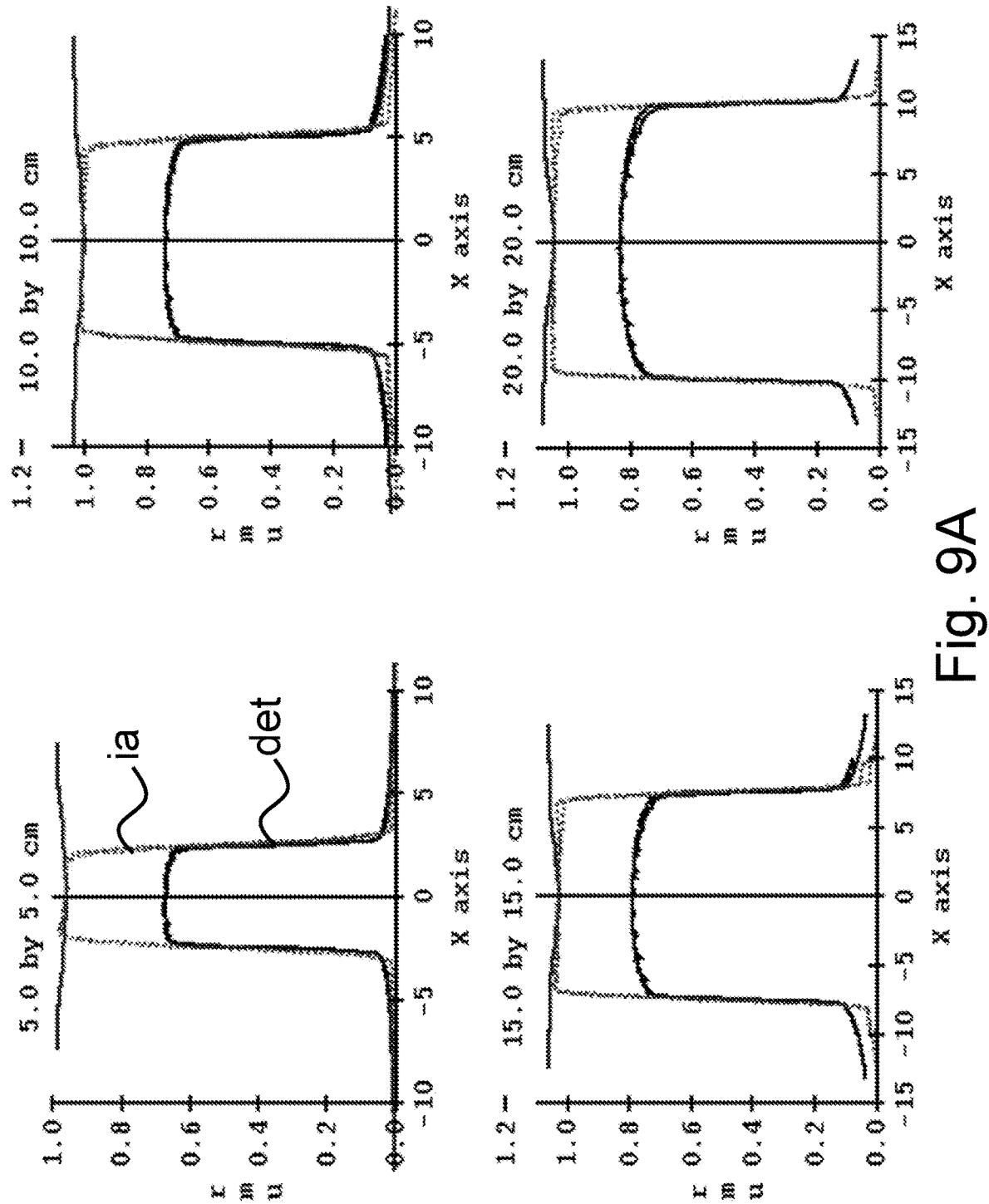
Figure 9B:
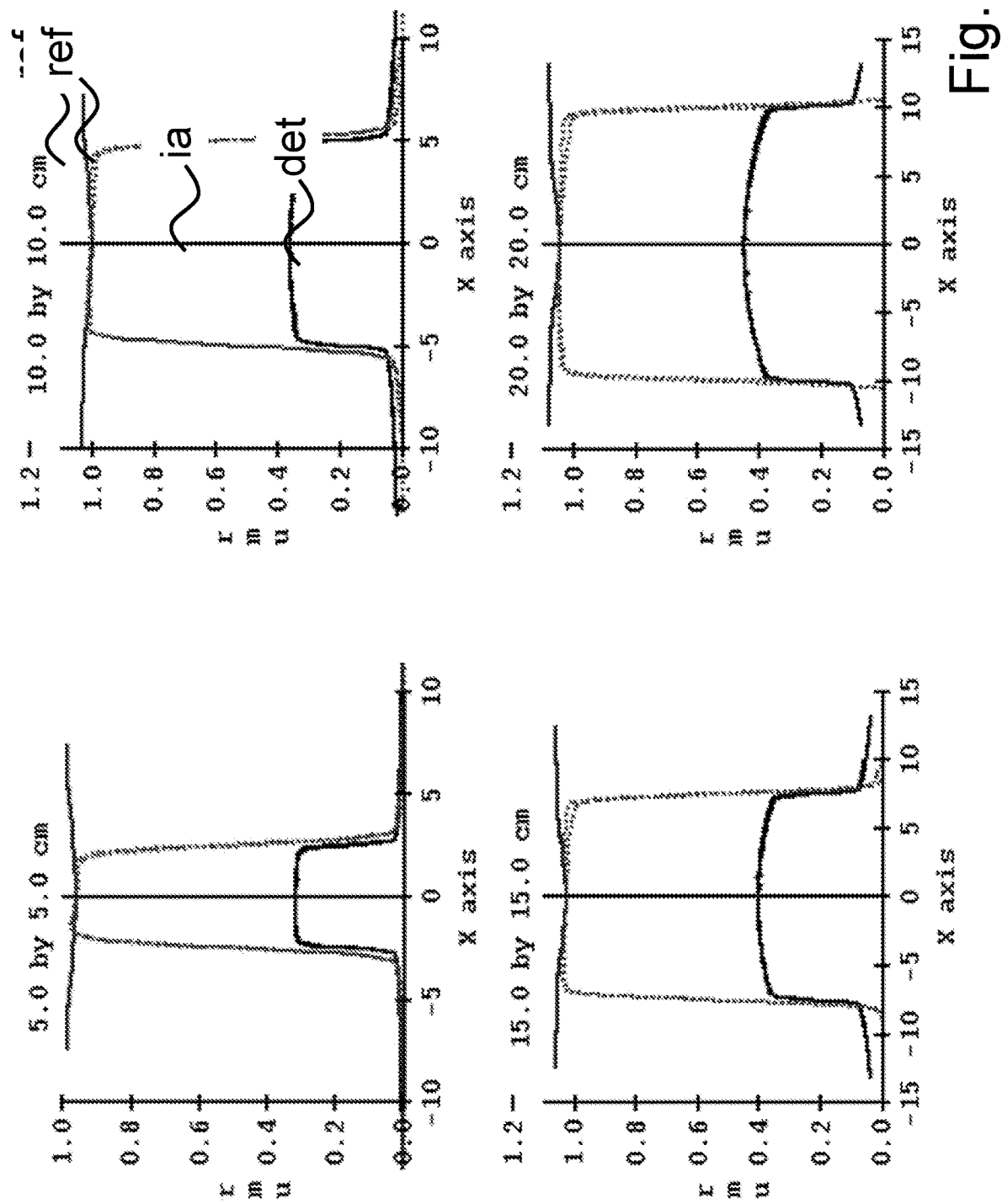
Figure 9C:
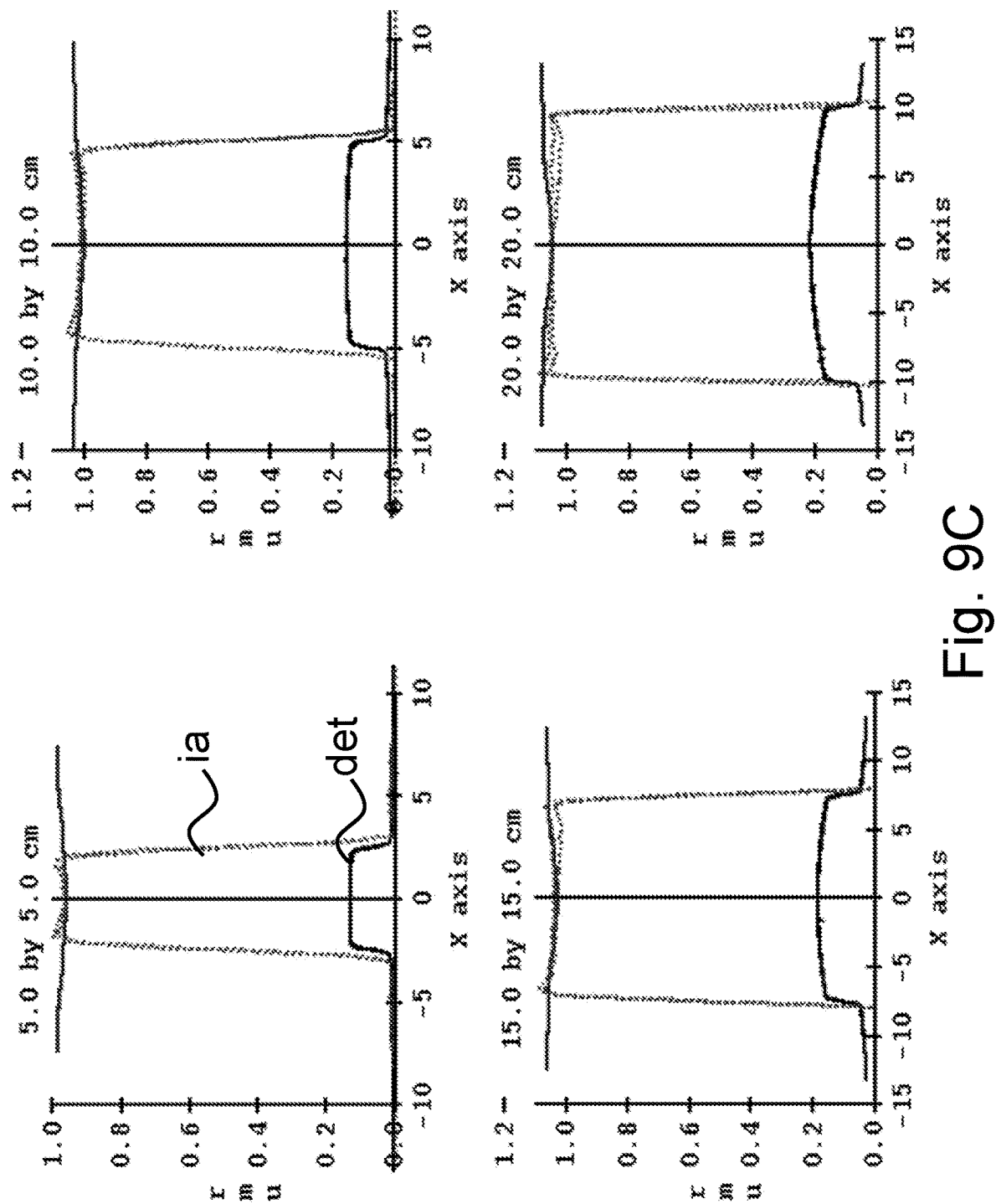

FIGS. 9A-9C illustratively show the various cases of in air radiation intensity fluence maps/profiles ia corresponding to the profiles of FIGS. 8A-8C, but with the corrective calibration applied to their generation. As shown, the in air radiation intensity fluence profile ia exhibits considerably greater correlation to the reference profile ref for each equivalent water thickness, across all illustrated radiation field sizes. Some drop off is observed at the 20×20 cm field size for certain water thicknesses, but such divergence from the reference profile ref is negligible in practice.

In those applications of the method disclosed herein where additional data is taken (such as at different image detector distances (24) or air gap distances (23)) to produce further sets of kernels for geometries that deviate from isocenter of the patient, suitable air gap correction measures are preferably taken to correct for different exit surface distances to the given EPID. As noted in preceding paragraphs, a change in exposure to the EPID typically occurs as a slow function of the air gap distance (23) between the exit surface of the phantom (2) and the EPID (3). When the EPID (3) is used at the distance at which EPID images were taken to fit the EPID deconvolution kernel, errors due to the isocenter not actually being aligned with the center of the patient will be minimal.

The potential effects of such air gap "errors" become more significant for larger fields sizes. A direct method is here described to correct for different air gap distances (25) due to either isocenter offset from the center of the patient, or use of the EPID (3) at a different distance (29). By normalizing data for each field size, differences are preferably employed rather than absolute values, so as to enhance accuracy and/or efficiency.

The variation of the EPID (3) signal with air gap distance (23) for a fixed field (21) and phantom thickness (26) is independent of the point response of the EPID (3) which is otherwise accounted for in the deconvolution process, as disclosed in FIG. 6. Hence, given a fixed field size (21) and thickness (26), the variation of signal with gap distance (23) may be measured and directly applied as a correction. This eliminates the need to execute a deconvolution with kernels measured for different air gaps and to then interpolate between those deconvolved images. Furthermore, signal variation versus air gap variation tends to yield a smooth curve which may be fitted to a second order polynomial and extrapolated to zero air gap distance (23). The scatter dose from the patient is governed by the inverse square law with the patient appearing as an extended source of radiation. The response of the EPID to the scatter radiation on the central axis is inherently accounted for when interpolation is made between the multiple output images from the deconvolution process (56). Extrapolation to larger air gaps may also be made until the minimum of the $2^{nd}$ order polynomial is reached, with the resulting value being used for larger air gaps as the curve flattens out with increased air gap distance.

This approach allows for a simple look-up of a correction factor for the air gap differing from the nominal value for which the EPID deconvolution kernels were fitted, which is given by the equation:

Air gap=EPID SID−(100.0 cm+0.5×thickness)

where EPID SID (Source-to-Image Distance) is fixed (24) for all the images acquired for fitting the kernels, and isocenter is aligned with the center of the water phantom (26). Further, there is likely to be little variation between EPIDs (3) of the same model in terms of signal change with air gap change (23 and 25), and one set of data may be applied to numerous machines.

EPID images are captured for a fixed set of field sizes (21) and water thicknesses (26), with a variable range of air gaps (23). For each field size and thickness, a $2^{nd}$ order polynomial is fitted to the signal versus air gap distance curve, such that a fixed range of signals for air gaps starting at zero may be computed from the fit. A three-dimensional air gap correction table indexed by field size, thickness, and air gap is directly generated from the data.

Example: Application to Clinical Exit Images

The data in this example includes images taken for a range of thickness, field size, and air gap. On a pixel-by-pixel basis, given particular values of the air gap distance (25) and thickness (22) at a pixel, and a field size to be defined below, a correction factor is interpolated from the corresponding three-dimensional air gap correction table and applied to that pixel value.

Clinical images, however, are not typically of square open field sizes. They tend to comprise modulated fields. The field size used to look up the correction factor must be generated by a suitable metric that accounts for the amount of scatter generated in the patient from the radiation field in such manner that different size square fields will generate different amounts of scatter. For each field image, the maximum intensity is determined, and all other pixels are divided by that maximum value. The pixels are then summed and multiplied by the area per pixel. A square root is then taken, and the result scaled (or, demagnified) as needed (such as to a distance of 100 cm). The field sizes used in the air gap table that is a function of air gap distance, thickness, and field size, are regenerated by this algorithm for consistency.

The air gap correction factor is the ratio of the result for the nominal air gap which the EPID kernels were generated with, divided by the result for the actual air gap in the clinical image at the particular pixel, and can be applied at operation (56) in FIG. 6.

Figure 7:
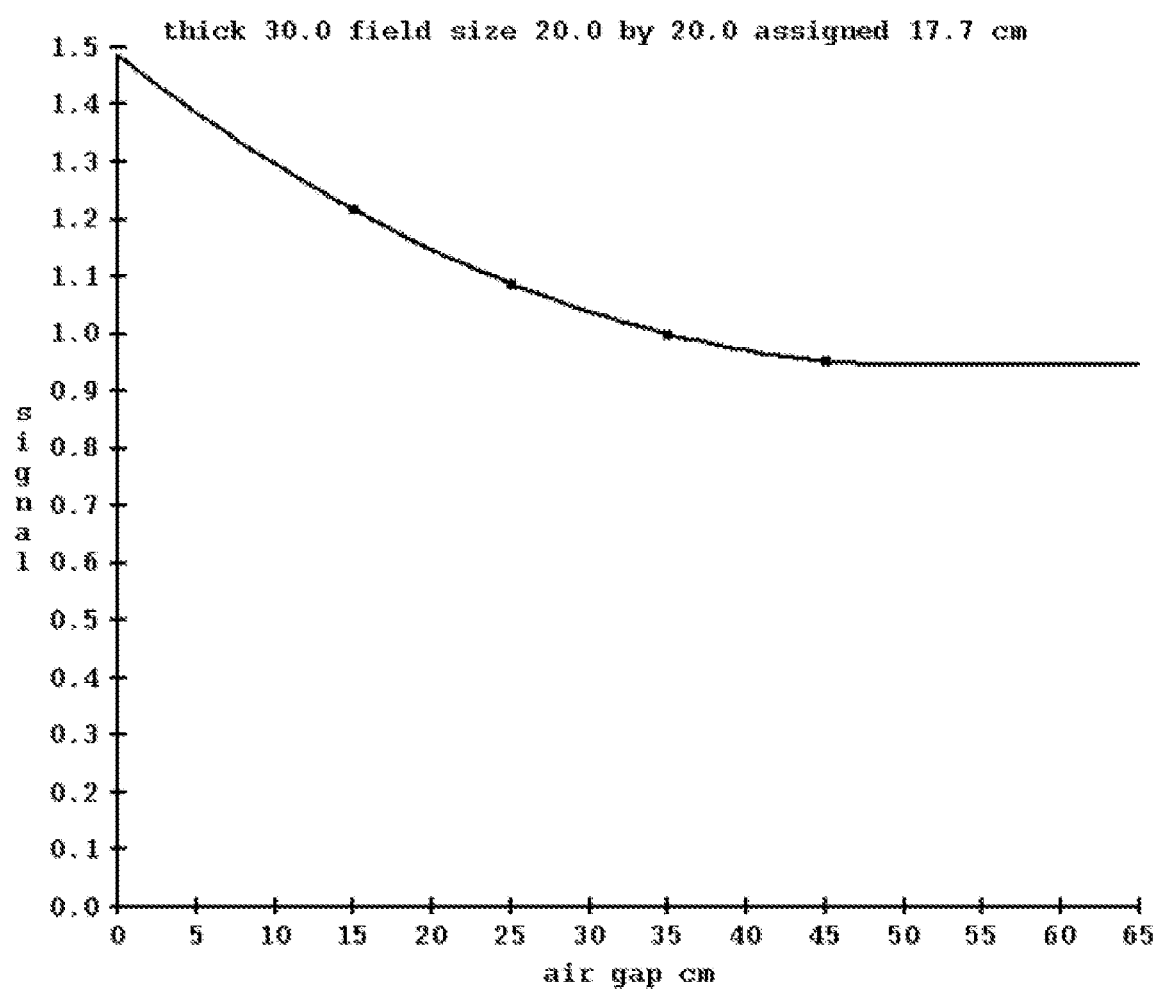
FIG. 7 is a schematic diagram illustrating a graphic plot of a curve fitted to characterize variation of a signal value with air gap variation.

Turning more specifically to a quantitative example, for each field size and thickness, a $2^{nd}$ order polynomial is fitted to the central axis signal value versus air gap. The curve is extrapolated to zero field size and extended in the other direction. Once the minimum of the resulting parabolic curve is reached, the curve just extends at that minimum. FIG. 7 illustrates an exemplary plot of a sample curve for a 30 cm thick, 20×20 cm field size.

As noted, the field size is preferably generated by a suitable metric that will account for the amount of scattering from the radiation field since modulated fields are not open square and rectangular fields. For each field image, the maximum intensity is found, and all other pixels are divided by that maximum intensity. The pixels are then summed, multiplied by the area of an individual pixel. A square root is then taken, and the result scaled (or demagnified) to as needed, for instance to a distance of 100 cm. In the example of FIG. 7, an equivalent field size of 17.7 cm was computed for the image of a 20×20 cm field (demagnified to 100 cm). While something of a loose metric, this provides a common measure for all radiation fields.

For any given thickness th, then, the curve is normalized to 1.0 for the air gap according to the equation:

Air gap=EPID SID−(100.0 cm+½th)

For 30 cm thickness and 150 cm SID, the normalization is to an air gap of 35 cm. In application, the data is renormalized to whatever SID was used for the EPID kernel data. It is therefore preferable for the EPID kernel images be taken so that the above equation generates the correct air gap for a given thickness. On a pixel-by-pixel basis, given the air gap, thickness, and field size, a correction factor is interpolated from the corresponding three-dimensional air gap correction table and applied to the given pixel value. Since the deconvolution has already accounted for the field size response of the EPID, the interpolated correction factor corrects for the change in intensity based on measured data due to a change in the air gap in the nominal measurement used to fit the exit EPID kernel.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method for optimized reconstruction of a treatment dose delivered to a patient during radiation therapy based on exit images captured therefrom, comprising:
   establishing a plurality of reference exit images measured on a detection plane by a first radiation detector through a phantom for a range of treatment field sizes and a range of water equivalent thicknesses for the phantom to emulate one or more patients;
   establishing a plurality of predetermined intensity references at the detection plane for the ranges of treatment field sizes and water equivalent thicknesses for the phantom;
   determining for each of the water equivalent thicknesses of the phantom a deconvolution kernel;
   capturing with the first radiation detector a plurality of exit images for a plurality of the treatment fields upon a patient during radiation therapy thereof, each exit image being defined by a plurality of detection points offset from a central axis of the detection plane by a corresponding radius, the detection points each having an exit image value associated therewith;
   defining for each detection point of each exit image at least one water equivalent path of radiation from a source to the detection point through the patient, the water equivalent path defined based upon predetermined image data established for the patient;
   executing deconvolution of each exit image with at least one deconvolution kernel to generate an in air radiation intensity fluence map corresponding thereto, the in air radiation intensity fluence maps being indicative of treatment dose to the patient;
   selectively executing adaptive calibration to generate a plurality of attenuation factors for at least a portion of the detection points of each exit image based on corresponding portions of the in air radiation intensity fluence map and predetermined intensity references;
   responsive to the execution of adaptive calibration, selectively feeding back the attenuation factors for application to each exit image and re-execution of the deconvolution thereon to generate final in air radiation intensity fluence map therefor; and,
   determining for each final in air radiation intensity fluence map of an exit image a corresponding contribution to the treatment dose delivered to the patient.

2. The method as recited in claim 1, further comprising execution of a base attenuation correction to apply a plurality of base attenuation factors to at least a portion of the detection points of each exit image, the base attenuation factors being generated based on at least one of the reference exit images for a water equivalent path corresponding to the exit image.

3. The method as recited in claim 1, wherein the predetermined intensity references are computed based on measurement on the detection plane by a second radiation detector through the phantom, the second radiation detector being greater in accuracy than the first radiation detector.

4. The method as recited in claim 3, wherein the second radiation detector includes an ion chamber device.

5. The method as recited in claim 3, wherein the adaptive calibration includes:
   for each treatment field size and each water equivalent thickness of the phantom, dividing the exit image values of the detection points by a predictive compensation factor;
   for each water equivalent thickness of the phantom, fitting a point spread function with respect to the exit image values of the detection points at each radius equaling one of the treatment field sizes, and computing in air radiation intensity fluence maps based thereon for a largest of the treatment field sizes; and,
   generating a set of attenuation curves for deriving the attenuation factors, the attenuation curves each indicating a degree of attenuation upon radiation transmission through the phantom over the range of water equivalent thicknesses thereof, the attenuation curves respectively corresponding to an incremental set of detection point radius values.

6. The method as recited in claim 5, wherein generation of the set of attenuation curves includes for each one of the detection point radius values in the incremental set:
   at each water equivalent thickness, computing a ratio of intensity between a radiation intensity for the detection point from the in air radiation intensity fluence map of the largest treatment field size, with respect to the predetermined reference intensity corresponding to the water equivalent thickness and said one of the detection point radius values;
   computing an average ratio of intensity for each of four diagonal segments of detection points, each diagonal segment including detection points disposed between the central axis and a corner position offset therefrom by said one of the detection point radius values along both of two dimensional axes defining the detection plane;
   generating for each water equivalent thickness at said one of the detection point radius values an attenuation data point based on the corresponding average ratio; and,
   fitting a sum of exponentials to a set of the attenuation data points for said one of the detection point radius values to generate the attenuation curve therefor.

7. The method as recited in claim 6, further comprising execution of a base attenuation correction to apply a plurality of base attenuation factors to at least a portion of the detection points of each exit image, the base attenuation factors being generated based on at least one of the reference exit images for a water equivalent path corresponding to the exit image; wherein responsive to execution of the adaptive calibration, the attenuation factors generated thereby are fed back to the base attenuation correction for re-execution with the base attenuation factors replaced by the attenuation factors.

8. The method as recited in claim 1, wherein the predetermined image data established for the patient includes a CT scan set captured for the patient.

9. A system for optimized reconstruction of a treatment dose delivered to a patient during radiation therapy based on exit images captured therefrom, comprising:
   a radiation source;
   a reference data acquisition portion operably coupled to the radiation source for establishing a plurality of reference exit images measured on a detection plane by a first radiation detector through a phantom for a range of treatment field sizes and a range of water equivalent thicknesses for the phantom to emulate one or more patients, the reference data acquisition portion determining for each of the water equivalent thicknesses of the phantom a deconvolution kernel;
   a radiation treatment imaging portion operably coupled to the radiation source, the radiation treatment imaging portion capturing with the first radiation detector a plurality of exit images for a plurality of the treatment fields upon a patient during radiation therapy thereof, each exit image being defined by a plurality of detection points offset from a central axis of the detection plane by a corresponding radius, the detection points each having an exit image value associated therewith;
   a data conversion portion coupled to the reference data acquisition and radiation treatment imaging portions for converting the exit images to corresponding in air radiation intensity fluence maps, each in air radiation intensity fluence maps being indicative of treatment dose to the patient, the data conversion system being configured to:
      define for each detection point of each exit image at least one water equivalent path of radiation from a source to the detection point through the patient, the water equivalent path defined based upon predetermined image data established for the patient;
      deconvolving each of the exit images with at least one deconvolution kernel to generate the in air radiation intensity fluence map corresponding thereto;
      selectively executing adaptive calibration to generate a plurality of attenuation factors for at least a portion of the detection points of each exit image based on corresponding portions of the in air radiation intensity fluence map and a plurality of predetermined intensity references defined at the detection plane for the ranges of treatment field sizes and water equivalent thicknesses for the phantom;
      responsive to the execution of adaptive calibration, selectively feeding back the attenuation factors for application to each exit image and re-execution of the deconvolution thereon to generate final in air radiation intensity fluence map therefor; and,
      determining for each final in air radiation intensity fluence map of an exit image a corresponding contribution to the treatment dose delivered to the patient.

10. The system as recited in claim 9, wherein the data conversion portion executes a base attenuation correction to apply a plurality of base attenuation factors to at least a portion of the detection points of each exit image, the base attenuation factors being generated based on at least one of the reference exit images for a water equivalent path corresponding to the exit image.

11. The system as recited in claim 9, wherein the predetermined intensity references are computed based on measurement on the detection plane by a second radiation detector through the phantom, the second radiation detector being greater in accuracy than the first radiation detector.

12. The system as recited in claim 11, wherein the second radiation detector includes an ion chamber device.

13. The system as recited in claim 9, wherein the adaptive calibration executed by the data conversion portion includes:
   for each treatment field size and each water equivalent thickness of the phantom, dividing the exit image values of the detection points by a predictive compensation factor;
   for each water equivalent thickness of the phantom, fitting a point spread function with respect to the exit image values of the detection points at each radius equaling one of the treatment field sizes, and computing in air radiation intensity fluence maps based thereon for a largest of the treatment field sizes; and,
   generating a set of attenuation curves for deriving the attenuation factors, the attenuation curves each indicating a degree of attenuation upon radiation transmission through the phantom over the range of water equivalent thicknesses thereof, the attenuation curves respectively corresponding to an incremental set of detection point radius values.

14. The system as recited in claim 13, wherein execution of the data conversion portion in generating the set of attenuation curves includes for each one of the detection point radius values in the incremental set execution:
   at each water equivalent thickness, computing a ratio of intensity between a radiation intensity for the detection point from the in air radiation intensity fluence map of the largest treatment field size, with respect to the predetermined reference intensity corresponding to the water equivalent thickness and said one of the detection point radius values;
   computing an average ratio of intensity for each of four diagonal segments of detection points, each diagonal segment including detection points disposed between the central axis and a corner position offset therefrom by said one of the detection point radius values along both of two dimensional axes defining the detection plane;
   generating for each water equivalent thickness at said one of the detection point radius values an attenuation data point based on the corresponding average ratio; and,
   fitting a sum of exponentials to a set of the attenuation data points for said one of the detection point radius values to generate the attenuation curve therefor.

15. The system as recited in claim 9, wherein the predetermined image data established for the patient includes a CT scan set captured for the patient.

16. A method for optimized reconstruction of a treatment dose delivered to a patient during radiation therapy based on exit images captured therefrom, comprising:
   establishing a plurality of reference exit images measured on a detection plane by a first radiation detector through a phantom for a range of treatment field sizes and a range of water equivalent thicknesses for the phantom to emulate one or more patients;
   establishing a plurality of predetermined intensity references at the detection plane for the ranges of treatment field sizes and water equivalent thicknesses for the phantom, the predetermined intensity references being computed based on measurement on the detection plane by a second radiation detector through the phantom, the second radiation detector being greater in accuracy than the first radiation detector;

determining for each of the water equivalent thicknesses of the phantom a deconvolution kernel;

capturing with the first radiation detector a plurality of exit images for a plurality of the treatment fields upon a patient during radiation therapy thereof, each exit image being defined by a plurality of pixels offset from a central axis of the detection plane by a corresponding radius, the pixels each having an exit image value associated therewith;

defining for each pixel of each exit image at least one water equivalent path of radiation from a source to the pixel through the patient, the water equivalent path defined based upon predetermined image data established for the patient;

executing deconvolution of each exit image with at least one deconvolution kernel to generate an in air radiation intensity fluence map corresponding thereto, the in air radiation intensity fluence maps being indicative of treatment dose to the patient;

selectively executing adaptive calibration to generate a plurality of attenuation factors for at least a portion of the pixels of each exit image based on corresponding portions of the in air radiation intensity fluence map and predetermined intensity references;

responsive to the execution of adaptive calibration, selectively feeding back the attenuation factors for application to each exit image and re-execution of the deconvolution thereon to generate final in air radiation intensity fluence map therefor; and, determining for each final in air radiation intensity fluence map of an exit image a corresponding contribution to the treatment dose delivered to the patient.

17. The method as recited in claim 16, further comprising execution of a base attenuation correction to apply a plurality of base attenuation factors to at least a portion of the pixels of each exit image, the base attenuation factors being generated based on at least one of the reference exit images for a water equivalent path corresponding to the exit image.

18. The method as recited in claim 17, wherein the adaptive calibration includes:

for each treatment field size and each water equivalent thickness of the phantom, dividing the exit image values of the pixels by a predictive compensation factor;

for each water equivalent thickness of the phantom, fitting a point spread function with respect to the exit image values of the pixels at each radius equaling one of the treatment field sizes, and computing in air radiation intensity fluence maps based thereon for a largest of the treatment field sizes; and, generating a set of attenuation curves for deriving the attenuation factors, the attenuation curves each indicating a degree of attenuation upon radiation transmission through the phantom over the range of water equivalent thicknesses thereof, the attenuation curves respectively corresponding to an incremental set of pixel radius values.

19. The method as recited in claim 18, wherein generation of the set of attenuation curves includes for each one of the pixel radius values in the incremental set:

at each water equivalent thickness, computing a ratio of intensity between a radiation intensity measured for the pixel, with respect to the predetermined reference intensity corresponding to the water equivalent thickness and said one of the pixel radius values;

computing an average ratio of intensity for each of four diagonal segments of pixels, each diagonal segment including pixels disposed between the central axis and a corner position offset therefrom by said one of the pixel radius values along both of two dimensional axes defining the detection plane;

generating for each water equivalent thickness at said one of the pixel radius values an attenuation data point based on the corresponding average ratio; and, fitting a sum of exponentials to a set of the attenuation data points for said one of the pixel radius values to generate the attenuation curve therefor.

20. The method as recited in claim 19, wherein the predetermined image data established for the patient includes a CT scan set captured for the patient.

* * * * *